(12) United States Patent
Ghazzi et al.

(10) Patent No.: US 6,740,648 B2
(45) Date of Patent: May 25, 2004

(54) TREATMENT OF PULMONARY HYPERTENSION

(75) Inventors: Maha Ghazzi, Ann Arbor, MI (US); Milton Lethan Pressler, Saline, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/970,211

(22) Filed: Oct. 3, 2001

(65) Prior Publication Data

US 2002/0128259 A1 Sep. 12, 2002

Related U.S. Application Data

(60) Provisional application No. 60/237,538, filed on Oct. 4, 2000.

(51) Int. Cl.[7] ............................................. A61K 31/55
(52) U.S. Cl. ............................................... 514/217
(58) Field of Search .................................. 514/217

(56) References Cited

U.S. PATENT DOCUMENTS

| | | | |
|---|---|---|---|
| 5,225,402 A | 7/1993 | Ogawa et al. | 514/23 |
| 5,258,510 A | 11/1993 | Ogawa et al. | 540/476 |
| 5,338,755 A | 8/1994 | Wagon et al. | 514/414 |
| 5,710,150 A | 1/1998 | Taniguchi et al. | 514/213 |
| 5,719,155 A | 2/1998 | Cho et al. | 514/253 |
| 5,723,606 A | 3/1998 | Tanaka et al. | 540/578 |

FOREIGN PATENT DOCUMENTS

| | | | |
|---|---|---|---|
| WO | 98/25901 | * | 6/1998 |
| WO | 00/48601 | * | 8/2000 |

OTHER PUBLICATIONS

Tahara et al., Journal of Pharmacology & Experimental Therapeutics, 282(1), 301–308 (1997).*

Goetz A E et al: "High–altitude pulmonary edema '2!" New England Journal of Medicine 1996 US., vol. 335, No. 3, 1996 pp. 206–207.

* cited by examiner

*Primary Examiner*—Phyllis G. Spivack
(74) *Attorney, Agent, or Firm*—Andrew J. Leon

(57) ABSTRACT

Disclosed is a method for treating pulmonary hypertension using a vasopressin antagonist.

2 Claims, 9 Drawing Sheets

Change in Inspiratory Crackles post IV Dose
Changes @ 12 hours vs. Baseline CV Exam

TREATMENT OF PULMONARY HYPERTENSION

This application claims the benefit of Provisional Application No. 60/237,538 filed Oct. 4, 2000.

FIELD OF THE INVENTION

This invention relates to vasopressin antagonists for use in treating pulmonary hypertension. Specifically, this invention relates to the use of conivaptan for treating pulmonary hypertension.

BACKGROUND OF THE INVENTION

Pulmonary hypertension (PH) is a condition of increased pulmonary vascular resistance and pulmonary arterial pressure which interferes with ventilation-perfusion relationships. PH typically is characterized by increased blood pressure (above 30 mm Hg systolic and 12 mm Hg diastolic) within the pulmonary circulation. There are two subsets of pulmonary hypertension: primary (idiopathic or "unexplained") and secondary. The secondary form is by far the more prevalent. The most common causes of secondary pulmonary hypertension are heart disease and lung disease. Regardless of the root cause of the pulmonary hypertension, the resistance (precapillary) vessels of the lungs undergo anatomic change that contributes to the progression of pulmonary hypertension. Pulmonary arterial hypertension secondary to acquired heart disease begins with a disorder of the left ventricle that leads to pulmonary venous hypertension followed by pulmonary arterial hypertension.

Arginine vasopressin, also known as antidiuretic hormone (ADH), is synthesized in the magnocellular neurosecretory cells of the paraventricular and supraoptic nuclei of the hypothalamus and stored in the posterior pituitary. There are 2 classes of AVP receptors, $V_1$ and $V_2$. There are 2 subclasses of $V_1$ receptors, namely $V_{1A}$ and $V_{1B}$. $V_{1A}$ receptors are found in the vasculature, and mediate the pressor response of AVP by increasing the contraction of blood vessels. Recent in vitro studies in the rat suggest that the lung contains the $V_{1A}$ receptor subtype. $V_{1A}$ receptors are also found on platelets, where they mediate platelet aggregation. $V_{1B}$ receptors are located in the anterior pituitary and mediate adrenocorticotropic hormone (ACTH) release. $V_2$ receptors are located in the collecting ducts of the kidney; they are coupled to aquaporine channels and modulate free water clearance. Arginine vasopressin is released into the circulation in response to an increase in plasma osmolality (mediated by osmoreceptors) or a decrease in plasma volume or blood pressure (mediated by baroreceptors). However, there are other stimuli for AVP release, including norepinephrine, angiotensin II, emotion, nausea and vomiting, and fever. Elevated levels of AVP have been reported in patients with cardiac failure, although its pathophysiologic role is unknown.

We have now discovered that the use of a vasopressin antagonist is effective in reducing pulmonary pressures in patients with pulmonary hypertension. A vasopressin antagonist is surprisingly effective in selectively reducing right sided pressures, including right atrial pressure and pulmonary artery systolic pressure, without affecting systemic hemodynamics. The unexpected selectivity of a vasopressin antagonist on pulmonary circulation would confer benefit in patients with pulmonary hypertension of primary or secondary cause. It is therefore an object of this invention to provide a method for treating pulmonary hypertension by administering a vasopressin antagonist.

SUMMARY OF THE INVENTION

The invention provides a method for treating pulmonary hypertension using a vasopressin antagonist. The vasopressin antagonist to be employed is any chemical compound that is effective in inhibiting the biological activity of any arginine vasopressin or antidiuretic hormone. Numerous compounds are known to be vasopressin antagonists, and any of such compounds can be utilized in the treatment of pulmonary hypertension according to this invention.

In a preferred embodiment, the vasopressin antagonist to be utilized is a condensed benzazepine compound, such as those described in U.S. Pat. No. 5,723,606, incorporated herein by reference. In a further preferred embodiment, the vasopressin antagonist is an imidazo benzazepine of the Formula I

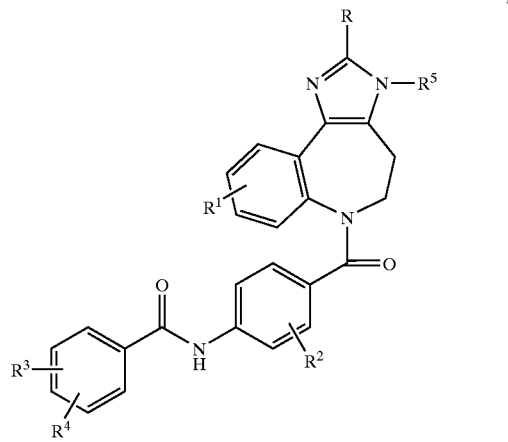

wherein R and $R^5$ are hydrogen or lower alkyl;

$R^1$, $R^2$, and $R^3$ independently are hydrogen, halogen, lower alkyl, lower alkoxy, amino, alkylamino, or dialkylamino; and $R^4$ is hydrogen, phenyl or substituted phenyl, and pharmaceutically acceptable salts thereof.

An especially preferred vasopressin antagonist to be used in accordance with this invention is conivaptan, which is N-[4-(2-methyl-4,5,6-tetrahydroimidazo[4,5-d][1] benzazepin-6-ylcarbonyl)phenyl]biphenyl-2-carboxamide hydrochloride. Conivaptan is also referred to as CI-1025 and YM087, and has the structural formula below

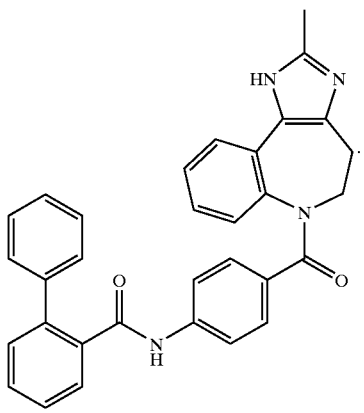

Conivaptan

Other vasopressin antagonists that can be employed according to this invention include the benzoheterocyclic compounds described in U.S. Pat. No. 5,258,510, incorporated herein by reference. Preferred compounds from this class to be used to treat pulmonary hypertension include the following:

5-Dimethylamino-1-[4-(2-methylbenzoylamino)-benzoyl]-2,3,4,5-tetrahydro-1H-benzazepine;

5-Dimethylamino-1-[2-chloro-4-(2-methylbenzoylamino)benzoyl ]-2,3,4,5-tetrahydro-1H-benzazepine;

5-Methylamino-1-[2-chloro-4-(2-methylbenzoylamino) benzoyl ]-2,3,4,5-tetrahydro-1H-benzazepine;

5-Cyclopropylamino-1-[2-chloro-4-(2-methylbenzoylamino)benzoxyl ]-2,3,4,5-tetrahydro-1H-benzazepine;

5-Cyclopropylamino-1-[2-chloro-4-(2-chlorobenzoylamino)benzoxyl ]-2,3,4,5-tetrahydro-1H-benzazepine;

5-Dimethylamino-1-[2-methyl-4-(2-methylbenzoylamino)benzoyl ]-2,3,4,5-tetrahydro-1H-benzazepine;

5-Dimethylamino-1-[2-methoxy-4-(2-methylbenzoylamino)benzoyl ]-1,2,3,4-tetrahydroquinoline;

7-Chloro-5-methylamino-1-[4-(2-methylbenzoylamino) benzoxyl ]-2,3,4,5-tetrahydro-1H-benzazepine; and 7-Chloro-5-methylamino-1-[4-(2-chlorobenzoylamino) benzoxyl ]-2,3,4,5-tetrahydro-1 H-benzazepine.

Other vasopressin antagonists that can be employed according to this invention include those described in U.S. Pat. Nos. 5,225,402; 5,258,510; 5,338,755; 5,719,155; and 5,710,150, all of which are incorporated herein by reference. Specific vasopressin antagonists include YM471, OPC-31260, OPC-21268, OPC-41061, SR-121463, SR-49059, VPA-985, CL-385004, FR-161282, JVT-605, VP-339, WAY-140288, and the like.

DETAILED DESCRIPTION OF THE INVENTION

Figure 1:
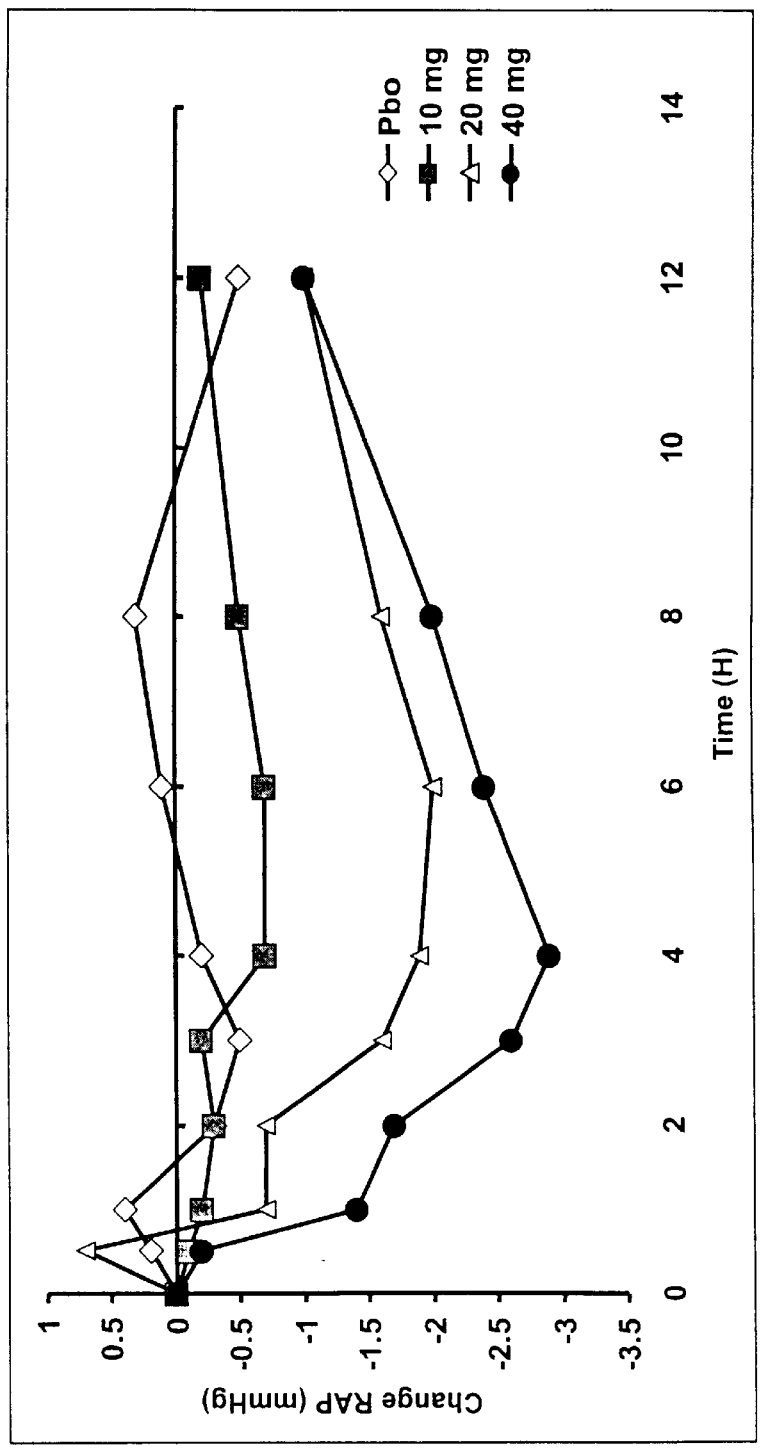
FIG. 1 shows the ability of conivaptan to reduce right atrial pressure (RAP).

As used herein, the terms "alkyl," "lower alkyl," or "$(C_1-C_{10})$-alkyl" mean a straight or branched hydrocarbon having from 1 to 10 carbon atoms and includes, for example, methyl, ethyl, n-propyl, isopropyl, n-butyl, sec-butyl, isobutyl, tert-butyl, n-pentyl, n-hexyl, and the like. The alkyl group can also be substituted (and thus may be referred to as "substituted alkyl") with one or more of the substituents listed below for phenyl.

By "alkoxy," "lower alkoxy," or "$(C_1-C_{10})$-alkoxy" in the present invention is meant straight or branched chain alkoxy groups having 1 to 10 carbon atoms, such as, for example, methoxy, ethoxy, propoxy, isopropoxy, n-butoxy, sec-butoxy, tert-butoxy, pentoxy, isopentoxy, neopentoxy, hexoxy, 2-hexoxy, 3-hexoxy, and 3-methylpentoxy.

By halogen in the present invention is meant fluorine, bromine, chlorine, and iodine, and their monovalent radicals.

The symbol "—" means a bond.

$R^4$ in Formula I can be phenyl or substituted phenyl, which is a phenyl group bearing 1, 2, or 3 substituents selected from alkyl, alkoxy, thio, alkylthio, hydroxy, halo, nitro, amino, alkyl, and dialkylamino, CN, $CF_3$, alkanoyl such as formyl and acetyl, and aryl groups such as furyl, thienyl, pyridyl, and the like. Typical substituted phenyl groups include 2-chlorophenyl, 3,4-dibromophenyl, 2-methyl-3-nitrophenyl, 3,5-dimethoxyphenyl, 2-fluoro-3-cyano-6-hydroxyphenyl, 3-acetylphenyl, and 4-dimethylamiophenyl.

The following abbreviations are used in the application.
CHF Congestive Heart Failure
NYHA New York Heart Association
CI Cardiac Index
PCWP Pulmonary Capillary Wedge Pressure
SBP Systolic Blood Pressure
AVP Arginine Vasopressin
ADH Antidiuretic Hormone
AVP and ADH are the same
PVR Pulmonary Vascular Resistance
SVR Systemic Vascular Resistance
RAP Right Atrial Pressure
PAs Pulmonary Artery Systolic Pressure
PAd Pulmonary Artery Diastolic Pressure
DBP Diastolic Blood Pressure
MAP Mean Arterial Pressure
LV Left Ventricular
CAD Coronary Artery Disease
LV-EF Left Ventricular Ejection Fraction
ACE Angiotensin Converting Enzyme $V_1$ A Class of Arginine Vasopressin Receptors
$V_{1A}$ A Specific Receptor Within $V_1$
$V_{1B}$ A Specific Receptor Within $V_1$
$V_2$ A Class of Arginine Vasopressin Receptors
RR Respiratory Rate
A-a Gradient Alveolar-arterial gradient oxygen The disclosures in this application of all articles and references, including patents, are incorporated herein by reference.

The compounds of Formula I are prepared in accordance with procedures known in the art. The starting materials and various intermediates of the vasopressin antagonists of Formula I may be obtained from commercial sources, prepared from commercially available organic compounds, or prepared using well-known synthetic methods.

As noted above, all that is required to practice this invention is to administer a vasopressin antagonist to a mammal suffering from pulmonary hypertension and in need of treatment. Any vasopressin antagonist can be used, and those skilled in medical care and pharmaceutical sciences are well aware of those compounds that are vasopressin antagonists. Moreover, such compounds can be readily identified by evaluation in common assays which measure vasopressin antagonist activity. Any such vasopressin antagonist will therefore be administered to a patient (eg, a human or an animal such as horses, cows, dogs, and cats) at a dose that is effective to treat the pulmonary hypertension. Such effective amounts will be from about 0.1 to about 1000 mg/kg, and typically from about 0.1 to about 250 mg administered once or twice a day.

The invention is illustrated further by the following studies that are not to be construed as limiting the invention in scope or spirit to the specific procedures or embodiments specifically described.

Preclinical pharmacologic studies have demonstrated potent binding of YM087 (conivaptan) to arginine vasopressin (AVP) receptors, causing antagonism of the vascular and renal effects of AVP. YM087 has high affinity for $V_{1A}$- and $V_2$-receptors with pKi (negative log of the binding inhibition constant) of 8.20 for human $V_{1A}$-receptors and 8.95 for human $V_2$-receptors (expressed in COS-1 cells).

EXAMPLE 1

Clinical Pharmacology

Conivaptan (YM087) has been given to approximately 250 healthy subjects who participated in a total of 15 Phase I studies (8 in Japan and 7 in Europe). Subjects taking oral medication received either a single dose of YM087 (dose range 0.2 through 120 mg) once daily (QD) or 30 or 120 mg YM087 administered as a divided dose twice daily (BID). Some subjects received YM087 as a single intravenous (IV) injection once daily over a dose range of 0.2 to 250 µg/kg or up to a maximum of 50 mg.

Inhibition of AVP-induced platelet aggregation (evidence of $V_{1A}$ antagonist activity) was seen in subjects who received YM087 at 20 mg/day orally or 2.5 mg IV. Total inhibition of AVP-induced dermal vasoconstriction was observed among subjects who received YM087 50 mg IV.

Normal subjects have demonstrated aquaretic action (evidence of $V_2$-receptor antagonism) accompanied by a decrease in urine osmolarity starting at 15 mg oral or 50 µg/kg IV. At higher doses aquaretic effects were more pronounced and at 120 mg QD or 60 mg BID given orally, or 50 mg given IV, were considered too uncomfortable to be tolerable. YM087 at IV doses up to 250 µg/kg and 50 mg/day increased urine production rate for up to 3 and 6 hours postdosing, respectively.

Safety

Among approximately 250 subjects treated, no major safety concerns were identified, and no drug-related serious adverse events were reported. The most frequent adverse events regardless of treatment association were mild or moderate thirst and mild headache. Other adverse events included flushes, sensation of cold extremities, abdominal complaints, abnormal stools, syncope, dizziness, palpitations, and postural hypotension. Three subjects who received YM087, and one who received placebo, developed minor, reversible leukopenia. No drug-related trend was observed in biochemical or hematological laboratory parameters. At higher doses, urinary osmolarity decreased and plasma osmolarity increased with or without an increase in plasma sodium. These observations were considered related to antagonism of $V_2$-receptors and not a safety concern. Vital signs (blood pressure and heart rate) were unaffected by YM087.

An objective of this study is to determine the dose-dependent effects of three different IV doses of YM087 on hemodynamic parameters in patients with severe congestive heart failure (NYHA Class III/IV).

It is another objective of the study to determine the safety of three different IV doses of YM087 in patients with severe congestive heart failure (NYHA Class III/IV).

It is yet another objective of the present study is to evaluate the relationship of YM087 IV dose and plasma concentrations to hemodynamic changes.

Study Design

This trial is a double-blind, placebo-controlled study of the intravenous dose response of YM087 on cardiopulmonary hemodynamics in patients with Class III/IV heart failure. A schematic of the study schedule is given in Table 1 below. Patients must be receiving background therapy of diuretics, ACE inhibitors, and optionally digoxin and/or β-blocker; patients are stratified as to whether they are receiving concomitant β-blocker treatment. Patients should take their daily dose of concomitant heart failure medications within 2 hours of catheter insertion. No additional doses of background heart failure medications should be administered during the study treatment phase. After insertion of a balloon-flotation pulmonary artery catheter, serial measurements are obtained over an 8-to 18-hour baseline and stabilization period. Patients meeting baseline eligibility criteria (CI≦2.6 L/min/m$^2$; PCWP≧16 mm Hg) after catheter stability is assured are administered an IV dose (30-minute infusion) of YM087 or placebo and monitored for the subsequent 12 hours.

Hemodynamic parameters and vital signs are measured at baseline during the 2 hours prior to drug administration and 30 minutes, 1, 2, 3, 4, 6, 8, and 12 hours after start of the IV infusion. A urethral catheter is placed and urine output is measured hourly for 2 hours prior until 12 hours post-study drug administration. Fluid intake is restricted to 250 mL every 2 hours (except at time of IV infusion) from time of insertion of a Swan-Ganz catheter and throughout the treatment period. YM087 plasma levels are determined at 1, 3, and 8 hours posttreatment. Serum electrolytes, BUN, creatinine, and serum osmolality are measured at baseline and 4 and 12 hours post treatment. Clinical laboratory and vasopressin plasma levels are measured at baseline and 12 hours post-drug administration. A numeric rating scale for assessing dyspnea is administered at baseline and 12 hours after study drug administration.

Study Schedule

TABLE 1-1

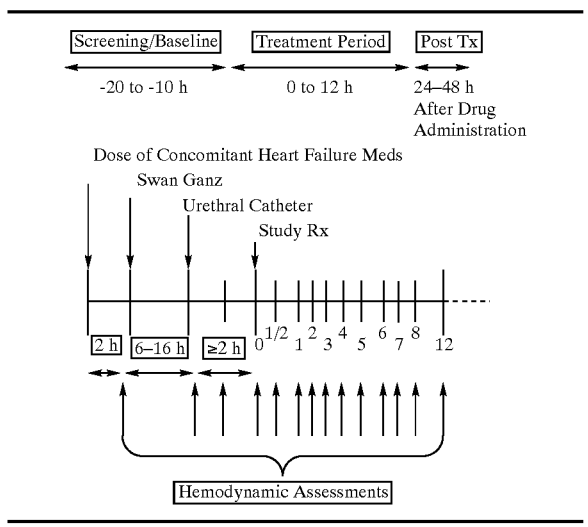

Screening and Baseline Phase (10–20 Hours) (See Table 1-1)

This phase allows the investigator to evaluate patients who may qualify for entry into the treatment period and to assess baseline values for a number of study parameters. An informed consent is signed. A medical history, physical examination, and assessment of NYHA functional class is done. Clinical laboratory parameters are measured. If left ventricular ejection fraction (LV-EF) is not measured during the previous 3 months, the patient undergoes radionuclide, contrast ventriculography, or 2-dimensional echocardiography to measure LV-EF.

Patients remain on stable doses of background heart failure medications throughout the baseline and treatment phase. Patients take a dose of their concomitant heart failure medications within 2 hours of Swan-Ganz catheter insertion. No additional dose of background medications is administered during the study treatment phase. After insertion of a balloon-flotation pulmonary artery catheter, several measurements of hemodynamic parameters are obtained over an 8-to 18-hour baseline and stabilization period. Patients meeting baseline eligibility criteria (CI$\leq$2.6 L/min/m$^2$; PCWP$\geq$16 mm Hg) on successive readings at least 30 minutes apart during 2 hours prior to study drug administration enter the treatment phase. Additional measurements of hemodynamic parameters over a larger baseline period (22 hours) are required to meet the reproducibility criteria. The two successive measurements of PCWP and CO are±10% and +15%, respectively, of the mean. Patients fast 6 hours prior to baseline measurements and remain fasting for the first 6 hours of the 12-hour treatment phase.

Patients who qualify for entry have blood drawn for a baseline assessment of clinical laboratory and vasopressin plasma levels. A urethral catheter is placed and urinary output measurements are obtained hourly for $\geq$2 hours prior to study drug administration and thereafter during the treatment phase. Hemodynamic measurements are obtained at least 30 minutes after insertion of the urethral catheter. Fluid intake is restricted to 250 mL every 2 hours (except at time of IV infusion) from time of insertion of a Swan-Ganz catheter and throughout treatment period. Vital signs are assessed at least every 4 hours. A numeric rating scale for assessing dyspnea are administered within 1 hour of study drug administration.

Treatment Phase

Patients meeting baseline eligibility criteria are randomized within an hour to receive double-blind IV bolus dose, administered over 30 minutes, of placebo or 1 of 3 doses of YM087 (10, 20, or 40 mg) in a 1:1:1:1 ratio. Patients refrain from taking concomitant heart failure medications during the 12-hour treatment period. Patients are stratified as to whether they are receiving concomitant treatment with a β-blocker. Hemodynamic parameters (cardiac output, intrapulmonary and systemic pressures) and vital signs are measured at 0.5, 1, 2, 3, 4, 6, 8, and 12 hours after start of the IV infusion. Clinical laboratory and vasopressin plasma levels are measured 12 hours postdose. YM087 plasma levels are determined at 1, 3, and 8 hours posttreatment. Serum electrolytes, BUN, creatinine and serum osmolality are measured at 4 and 12 hours posttreatment. Hourly urine output measurements are obtained during the entire 12-hour treatment phase. The numeric rating scale for assessing dyspnea is administered 12 hours postadministration of study medication.

Posttreatment Phase (24–48 Hours) After Administration of Study Medication

Patients return for an outpatient follow-up visit at least 24 to 48 hours after administration of study medication. Patients are followed for clinical assessment of adverse events. Clinical laboratory parameters are measured. Background heart failure medications are readjusted if necessary for safety/tolerance of the patient.

Study Population

All patients enrolled into this study have NYHA Class III/IV heart failure due to systolic LV dysfunction.

Source and Number of Patients

A total of 140 patients (35 per treatment group) are enrolled at 20 study centers. Each site is expected to enroll 6 to 8 patients. Enrollment is competitive and will stop when the study is complete.

Patient-Selection Criteria

Inclusion Criteria

Patients acceptable for inclusion into the study meet the following criteria:

1. Males or females 18 to 80 years of age; females are postmenopausal, surgically sterilized, or practicing a suitable method of birth control so that in the opinion of the investigator, they will not become pregnant during the study;
2. Symptomatic heart failure with Class III/IV functional impairment by New York Heart Association criteria;
3. Current therapy for heart failure consisting of at least 1 month duration of an ACE inhibitor, loop diuretic, and optionally digoxin and/or β-blocker;
4. Cardiac index $\leq$2.6 L/min/m$^2$, and pulmonary capillary wedge pressure $\geq$16 mm Hg on successive readings at least 30 minutes apart prior to study drug administration; and
5. Signed informed consent.

Exclusion Criteria

Presence of any of the following conditions excludes the patient from being eligible for study:

1. Breast feeding or pregnant;
2. Patients with supine systolic blood pressure<95 mm Hg or uncontrolled hypertension;
3. Patients with more than 2+edema (above the knee);
4. Uncontrolled symptomatic brady- or tachyarrhythmias (eg, sinus arrest; second-degree Mobitz type II or third-degree AV block, atrial fibrillation or flutter, frequent runs of ventricular tachycardia); patients with dual chamber pacemakers and/or implantable defibrillators are eligible, if the device has been implanted >60 days prior to screening;
5. Unstable angina pectoris and/or acute myocardial infarction within 1 month of baseline-;
6. Patients with severe COPD (FVC $\leq$1.5 L; FEV1 $\leq$1.0 L) or primary pulmonary hypertension;
7. Patients with significant uncorrected primary valvular disease or uncorrected congenital heart disease, for example, aortic stenosis (AVA <0.8 $cm^2$), mitral stenosis (MVA <1.2 $cm^2/m^2$), severe valvular insufficiency requiring valve replacement;
8. Patients with obstructive cardiomyopathy;
9. Patients with active myocarditis, constrictive pericardit's, untreated hypothyroidism or hyperthyroidism, adrenal insufficiency, active vasculitis due to collagen vascular disease, or other correctable nutritional or metabolic causes for heart failure;
10. Alanine aminotransferase (ALT) and aspartate aminotransferase (AST) elevations >3 times the upper limit of normal (ULN) reference range and/or bilirubin $\geq$mg/dL;
11. Patients with significant renal impairment, serum creatinine>2.5 mg/dL or creatinine clearance>30 mL/min;
12. Serious hematological diseases (eg, severe anemia, Hgb<10 g/dL: leukopenia, white blood cell [WBC] >4000/gL);
13. Active cancer within 5 years of screening for this study (exclusive of localized skin cancer or localized prostate cancer);
14. Patients on continuous and/or daily doses of IV inotropic drugs (eg, dobutamine; dopamine, milrinone, anrinone, etc) or parenteral vasodilators (eg, nitroprusside; nitroglycerin) within 7 days of screening;
15. Clinical evidence of digitalis toxicity;
16. Current illicit drug use or alcoholism;
17. Any concurrent illness which, in the opinion of the investigator, may interfere with treatment, evaluation of safety, and/or efficacy;
18. Participation in another clinical trial of an investigational drug (including placebo) within 30 days of screening for entry into the present study; or
19. Inability to understand and sign the Informed Consent to participate in this study.

Prohibited/Allowable Medications or Precautions

To minimize confounding factors and bias in interpreting results related to potential cardiac changes not associated with natural progression of CHF, concurrent heart failure medications are held stable throughout the treatment phase of the study. Changes in concurrent medications are made where issues of patient safety are evident.

Nonsteroidal anti-inflammatory agents (NSAIDS) are discouraged due to their inhibitory effects on renal function.

Permitted medications include those used to treat coronary artery disease (CAD), hypertension, diabetes, hyperlipidemia, and CHF. Heart failure medications can include ACE inhibitors, diuretics, digoxin, β-blocker, and intermittent oxygen. No other parenteral vasodilators (eg, nitroprusside, nitroglycerin) nor initiation of inotropic agents are allowed. Chronic low dose (<300 mg QD) amiodarone is permissible but not sotalol, dofetilide or other Class III antiarrhythmic agents. Calcium channel blockers with negative inotropic effects (eg, verapamil, diltiazem) are prohibited.

Patients enrolled in this study cannot be participating in any other ongoing protocol studying the effects of investigational medications.

Meals and Fluid Intake

Patients fast at least 6 hours prior to baseline hemodynamic measurements and must remain fasting during the first 6 hours of the 12-hour treatment phase. Fluid intake is restricted to 250 mL every 2 hours (except at time of IV infusion of study medication) from time of insertion of a Swan-Ganz catheter and throughout the treatment period.

Study Methodology

Efficacy Parameters

Primary Efficacy Parameter

Peak change from last baseline measurement in PCWP at 3 to 6 hours after start of study medication infusion as compared to placebo. Other characteristics of response profile (area under the PCWP/time curve) are defined in statistical analysis section of the protocol.

Secondary Efficacy Parameters

Peak change from last baseline measurement at 3 to 6 hours after start of study medication infusion as compared to placebo in:
1. Cardiac index (CI);
2. Pulmonary vascular resistance (PVR);
3. Systemic vascular resistance (SVR).

Other characteristics of response profile (CI, PVR, SVR) are defined in the statistical analysis section of the protocol (area under the curve).

Changes in urine output over time as compared to baseline.

Descriptive statistics for RA, PAs, PAd, BP, and HR are be performed.

Change from baseline in numeric rating scale for assessing dyspnea at 12 hours after administration of study medication.

Other Assessments

Pharmacokinetic/Pharmacodynamic Analysis

Plasma concentrations of YM087 are measured at 1, 3, and 8 hours after start of IV infusion of study medication using a validated LC/MS/MS method. Assay sensitivity, specificity, linearity, and reproducibility are determined before analysis of samples. The relationship between the primary efficacy parameters and plasma concentrations of YM087 including the interindividual variability are evaluated using appropriate pharnacostatistical methods.

Neurohormonal Assessments

Vasopressin plasma levels are measured at baseline and 12 hours after start of IV infusion of study medication.

Study Medication

Description

Study medication is provided to the study site as open-label, 5-mL ampoules not specifically assigned to patient or visit. Each ampoule will contain 5 mg/mL of YM087. The medication is prepared by an unblinded person. The investigator and study coordinator is blinded. YM087 (25 mg/5 mL) ampoules are stored in boxes protected from light at ambient temperature (15° C.–30° C.). An adequate number of ampoules are supplied to each site to complete the study. A detailed set of study medication preparation, dispensing, and administration instructions is provided with the initial shipment of study medication.

Dosing Procedure

YM087 sterile injection is added to a 50-mL bag containing D5W. Table 2-1 specifies the amount of YM087 for injection to dilute into D5W in order to achieve the desired dose. The contents of the bag are administered to the patients via a pump infusion system (eg, IMED™IVAC™) over 30 minutes.

TABLE 2-1

YM087 Dose Administration

| Dose (mg) | Volume of YM087 (mL) | Volume of D5W Added (mL) | Total Volume in Bag (mL) | Concentration (mg/mL) | Infusion Rate Over 30 Minutes (mL/min) |
|---|---|---|---|---|---|
| 10 | 2 | 8 | 60 | 0.167 | 2 |
| 20 | 4 | 6 | 60 | 0.333 | 2 |
| 40 | 8 | 60 | 60 | 0.667 | 2 |

Statistical Analysis and Rationale
Power and Sample Size

For this study, a total of 140 patients are considered with 35 patients in each of the 4 treatment groups (placebo, 10, 20, and 40 mg). The power to detect a difference of 3 mm Hg in the PCWP peak change from baseline within 3 to 6 hours after treatment administration, between placebo and any of the 3 active treatments, is determined using the formula for the power of the t-test (Lachin J. M., *Controlled Clinical Trials* 1981 ;2:93–113). Adjustment for multiple comparisons with placebo is performed using Dunnett's approach (Dunnett C. W., *Biometrics* 1964;20:482–91). Assuming a 15% dropout rate, an overall error rate of 0.05 two-sided, and a standard deviation of 3 mm Hg for the PCWP peak change, the power to detect a difference of 3 mm Hg between placebo and any of the YM087 groups is 93.6%. However, if a standard deviation of 4 mm Hg is assumed, the power becomes 71.1%.

Efficacy Parameters

Hemodynamic data in clinical trials of congestive heart failure is usually assessed by evaluating the differences in change from baseline to peak response among treatment groups. Generally, peak response is defined as an average of measurements taken at pre-specified hours (eg, at 2,3, and 4 hours) (Katz S. D. et al., *American Heart Journal* 1992; 123(1):95–103).

For this study, hemodynamic efficacy parameters of PCWP, CI, SVR, and PVR are evaluated in terms of their response profile. The response profile is assessed in terms of peak change, and area under the curve (AUC) delimited by the parameter change from baseline and measurement times. The peak change is defined as the maximum change from baseline, within the 3 to 6 hours after treatment administration, in the hemodynamic parameter of interest. The baseline value is considered the last acceptable measurement taken before treatment administration. The AUC is determined using the "linear trapezoidal rule," which delimits areas of each trapezoid by: two points on the graph of change from baseline against time, perpendiculars from the points to the X-axis, and the X-axis are summed up to get AUC. If measurements are missing at certain times, the AUC are calculated using all other available observations. Dose response over the treatment groups are assessed for selected measures.

The primary efficacy parameter for this study is peak change from baseline in PCWP. The secondary parameters are peak change from baseline in CI, SVR, and PVR. Changes in RA and PA pressures also are characterized. In addition, changes in urine output are characterized.

Analysis of the Primary Efficacy Parameter

An analysis of covariance (ANCOVA) model are used as the primary analysis to compare each of the YM087 doses with placebo in terms of peak change in PCWP (as defined above). The model will include effects due to treatment, center, an indicator variable for the presence or absence of β-blocker therapy, and possibly the baseline value as a covariate. Treatment-by-center and treatment-by-baseline interactions are investigated. All randomized patients that have a baseline measurement and at least one follow-up measurement are considered for this analysis. If there is only one observation within 3 to 6 hours, then the peak change is calculated using that observation and the baseline value. If there are no measurements in the 3 to 6 hour window, the last measurement prior to hour 3 is carried forward and used to calculate peak.

A secondary analysis of the AUC is conducted to support the primary analysis. For the area under the PCWP change from baseline and time curve, the analysis are conducted using ANCOVA in a similar manner as described for the primary analysis. The model will include effects due to treatment, center, an indicator variable for the presence or absence of β-blocker therapy, and possibly the baseline value as a covariate. Treatment-by-center and treatment-by-baseline interactions are investigated. All randomized patients that have a baseline and at least one follow-up measurement are considered for this analysis.

In order to claim positivity, results from the primary analysis for peak change in PCWP should be significant at the ax level corresponding to 0.049 using Dunnett's approach, or results from the secondary analysis of AUC at the 0.001 level. A supportive secondary trend analysis for dose response is also performed. Also, repeated measures ANCOVA are performed for selected measurements of the response profile.

Analysis of the Secondary Efficacy Parameters

The primary analysis for the secondary efficacy parameters of CI, SVR, and PVR are performed using ANCOVA as described for the primary efficacy parameter, to compare the treatment groups with placebo in terms of their peak change from baseline (as defined above). Patients are considered for this analysis according to the criteria described for the primary parameter. The significance levels are adjusted for multiple comparisons with placebo using Dunnett's method.

Analysis of the AUC and trend analysis is considered supportive, and conducted in the same manner as described for the primary parameter. Repeated measures ANCOVA are performed for selected measurements of the response profile. All randomized patients with a baseline and at least one follow-up measurement are considered.

The secondary parameter of urine output is summarized at baseline, and each collection time. In addition, a numeric rating scale is used for assessing dyspnea. The corresponding change from baseline for these parameters is summarized. Descriptive summaries include mean, standard error, median, minimum, and maximum. Other concurrently measured hemodynamic parameters (ie, RA, PAs, PAd, cuff SBP, cuff DBP, calculated MAP, and HR) is also summarized.

Results and Discussion

The results of the study show that the use of a vasopressin antagonist is effective in reducing pulmonary pressures in patients with pulmonary hypertension.

Figure 2:
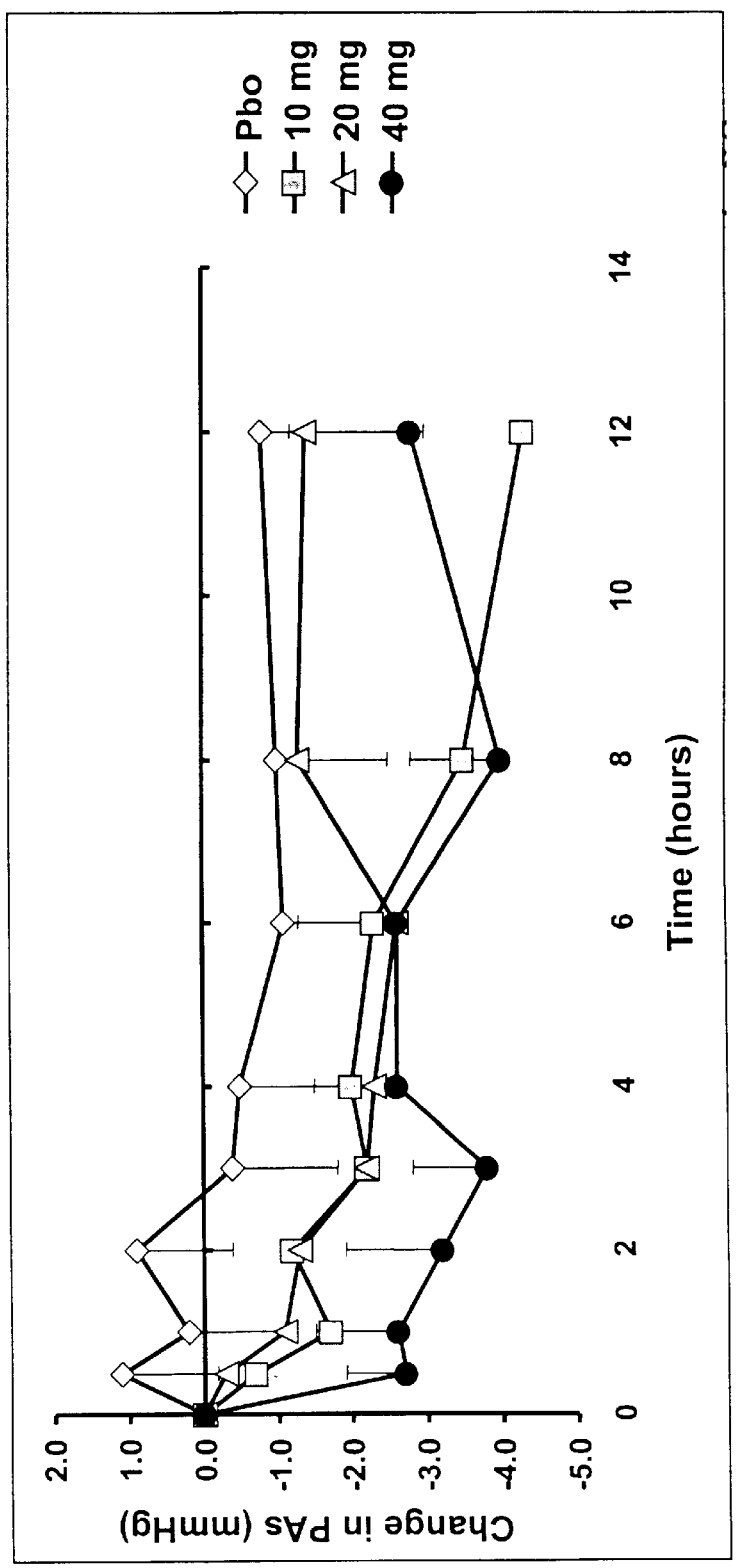
FIG. 2 shows the ability of conivaptan to reduce pulmonary artery systolic pressure (PAS).
Figure 3:
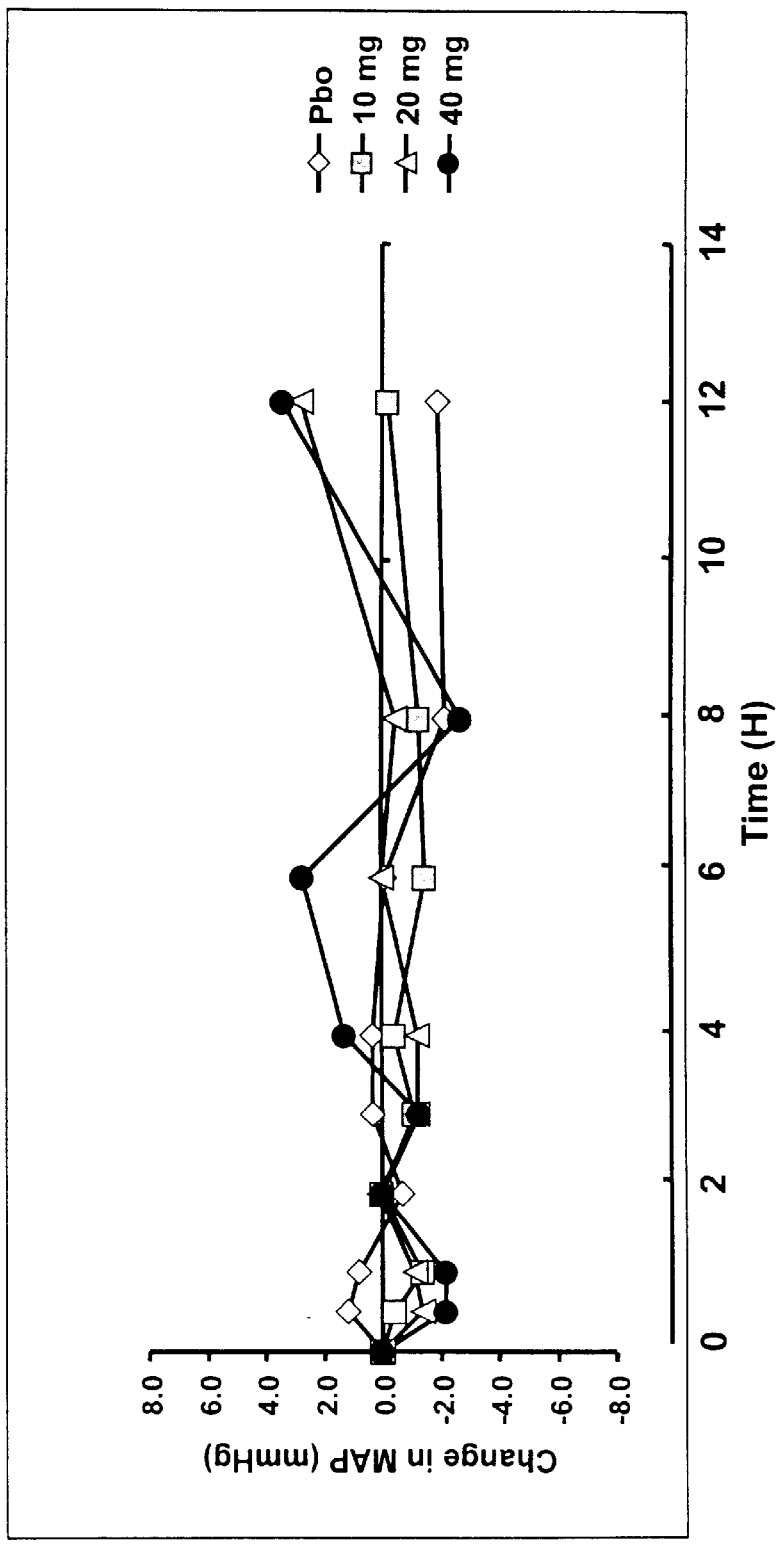
FIG. 3 shows that conivaptan has no effect on mean arterial pressure (MAP).
Figure 4:
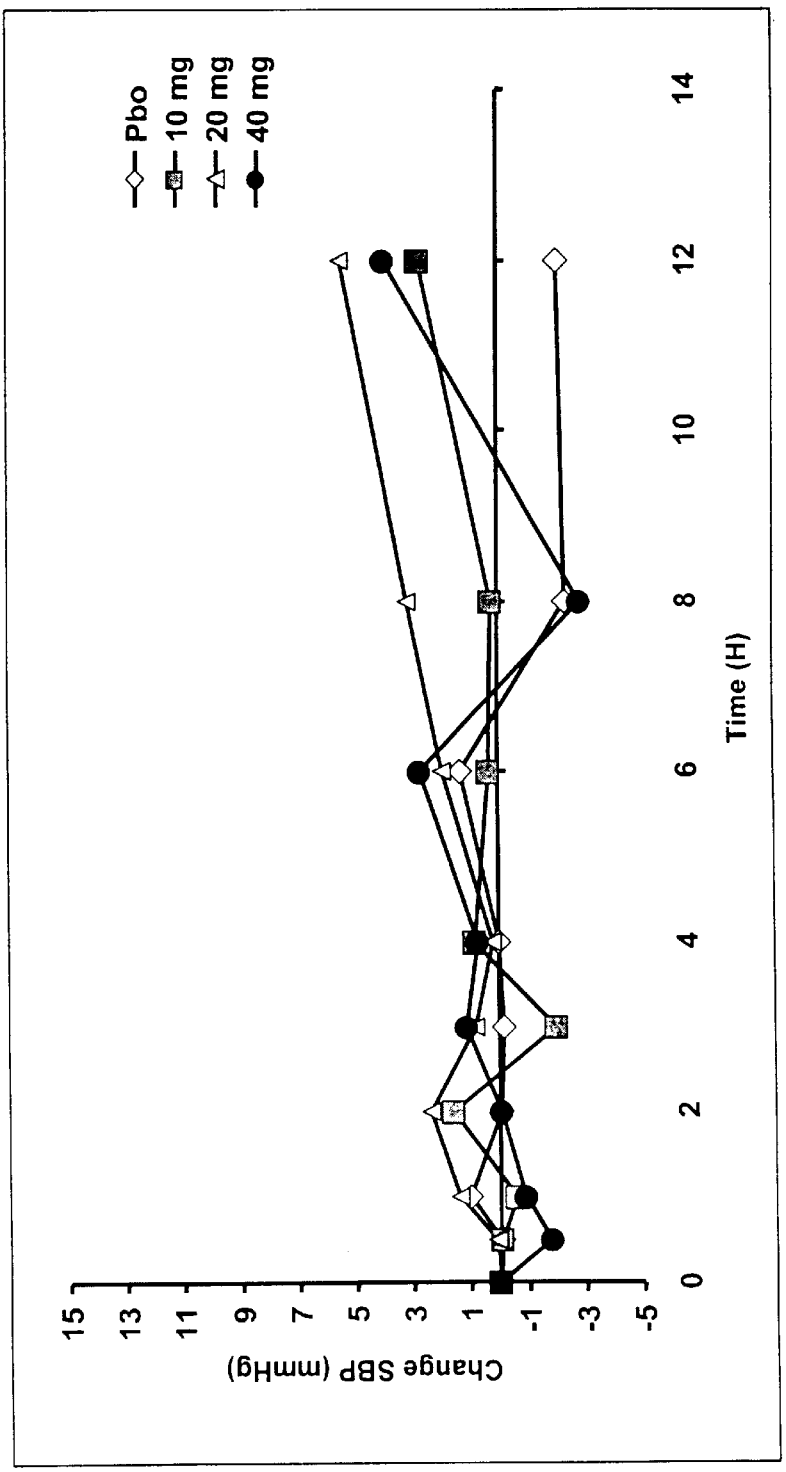
FIG. 4 shows the that conivaptan has no effect on systolic blood pressure (SBP).
Figure 5:
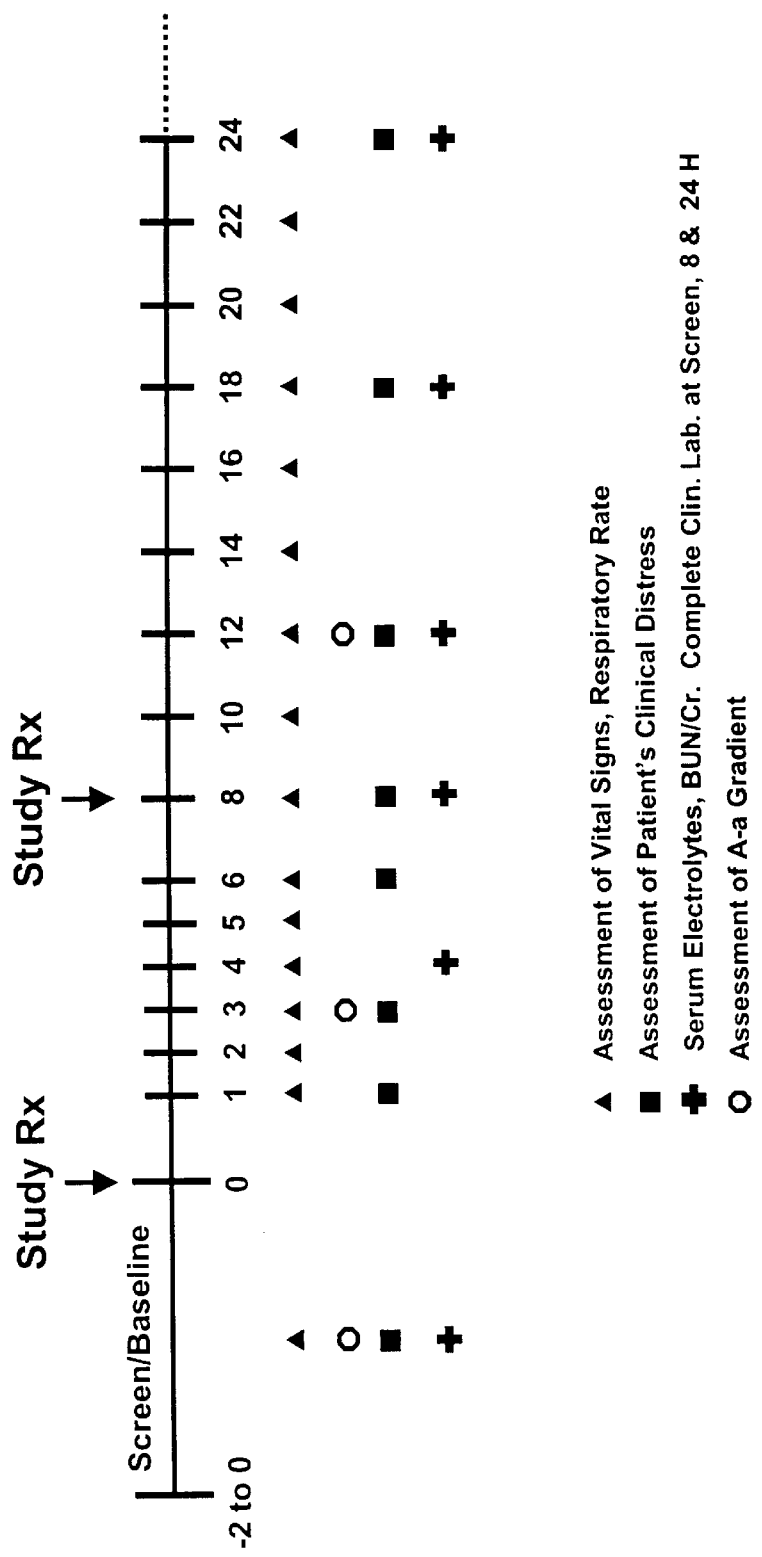
FIG. 5 study design—placebo controlled randomized to investigate the effects of the vasopressin antagonist on several measures of pulmonary congestion.
Figure 9:
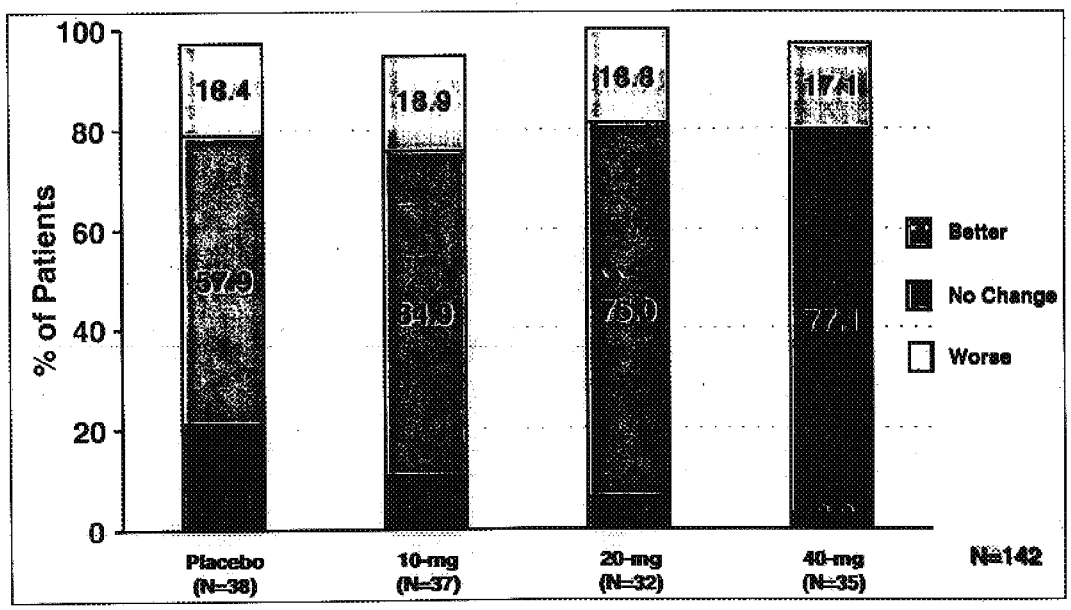
FIG. 9 demonstrates that fewer patients on conivaptan had worsened inspiratory crackles compared to placebo.

Hemodynamic assessments are obtained at baseline and at 0.5, 1, 2, 3, 4, 6, 8, and 12 hours after administration of study medication. The data shown in FIGS. 1–4 and 9 establish that a vasopressin antagonist reduces right atrial pressure (FIG. 1) and pulmonary artery systolic pressure (FIG. 2). At the 40 mg dose, conivaptan reduced RAP by as much as 3-mm Hg (FIG. 1), and reduced PAs by as much as 4-mm Hg (FIG. 2). Changes in inspiratory crackles post IV dose of 10, 20, 40 mg conivaptan were compared to placebo. The data shown in FIG. 9 demonstrates that fewer patients on conivaptan had worsened inspiratory crackles compared to placebo. There is no effect on systemic hemodynamics. There is no effect on mean arterial pressure (FIG. 3) and no effect on systolic blood pressure (FIG. 4). These results are surprising in that the vasopressin antagonist is selective in reducing right-sided pressures without affecting systemic hemodynamics. The unexpected selectivity of a vasopressin antagonist on the pulmonary circulation would confer benefit in patients with pulmonary hypertension of primary or secondary cause.

EXAMPLE 2

Clinical Pharmacology

Conivaptan (YM087) has been given to approximately 250 healthy subjects who participated in a total of 15 Phase 1 studies (8 in Japan and 7 in Europe). Subjects taking oral medication received either a single dose of YM087 (dose range 0.2 through 120 mg) once daily (QD) or 30 or 120 mg YM087 administered as a divided dose twice daily (BID). Subjects received YM087 as a single IV injection once daily over a dose range of 0.2 to 250 µg/kg or up to a maximum of 50 mg.

Inhibition of AVP-induced platelet aggregation (evidence of $V^{1A}$ antagonist activity) was seen in subjects who received YM087 at 20 mg/day orally or 2.5 mg IV. Total inhibition of AVP-induced dermal vasoconstriction was observed in subjects who received 50 mg IV. Normal subjects have demonstrated aquaretic action (evidence of $V_2$ receptor antagonism) accompanied by a decrease in urine osmolarity starting at 15 mg oral or 50 µg/kg IV. At higher doses aquaretic effects were more pronounced and at 120 mg QD or 60 mg BID given orally or 50 mg given IV were considered too uncomfortable to be tolerable in normal subjects. YM087 at IV doses up to 250 µg/kg and 50 mg/day increased urine production rate for up to 3 and 6 hours postdosing, respectively.

Safety

Among approximately 250 subjects treated, no major safety concerns were identified; one patient with severe heart failure sustained a grand mal seizure that was possibly related to YM087 at 40 mg BID. The most frequent adverse events regardless of treatment association were mild or moderate thirst and mild headache. Other incidental adverse events included flushes, a sensation of cold extremities, abdominal complaints, abnormal stools, syncope, dizziness, palpitations, and postural hypotension. Three subjects who received YM087 and one who received placebo developed minor, reversible decrease in white blood cell counts. No drug-related trend was observed in biochemical or hematological laboratory parameters. At higher doses, urinary osmolarity decreased and plasma osmolarity increased with or without an increase in plasma sodium. These observations were considered related to antagonism of $V_2$-receptors and not a safety concern. Vital signs (blood pressure and heart rate) were unaffected by YM087.

Study Objective(s)

An objective of this study is to explore the effectiveness of YM087 on relief of symptoms of pulmonary congestion in patients with acute decompensated heart failure; and it is another objective of this study to explore the safety of YM087 in patients with acute decompensated heart failure.

Study Design

This trial is an exploratory double-blind, placebo-controlled study of the safety and efficacy of YM087 20 mg administered twice (8 hours apart) over a 24-hour period as a 30-minute intravenous infusion versus placebo. A schematic of the study schedule is given in Table 1-2 below. The trial explores the effect on relief of pulmonary congestion in patients with a history of NYHA Class II–IV heart failure hospitalized in a monitored unit for acute decompensated heart failure. Patients may be on background therapy optionally with ACE-inhibitors, diuretics, digoxin, and β-blockers as long as these medications (excepting diuretics) were initiated prior to admission. On arrival to the hospital, the patient was assessed for enrollment criteria. If the criteria are met, consent was obtained and the patient enrolled. Patients needing treatment with a parenteral inotropic agent (eg milrinone; dobutamine) or who are intubated are excluded. Respiratory rate will be measured. Clinical laboratory parameters are measured if not assessed within 2 hours of screening. Once consented, the patient's clinical distress was assessed by vital signs, the Acute Heart Failure Score, the Physician/Study Coordinator Clinical Assessment Scale for patient's respiratory and global status, and the Patient Visual Analog Scale for respiratory and global status. Patients are administered 100% oxygen for 5 to 10 minutes and blood gases then drawn to assess A-a gradient. The baseline respiratory rate was measured 5 minutes prior to administration of study medication (must be ≧24 to meet inclusion criteria). The patient was randomized to treatment with 20 mg of YM087 or placebo administered as a 30-minute IV infusion on 2 occasions 8 hours apart. All patients received usual care at the discretion of the investigator including IV loop diuretics, oxygen, morphine, and IV vasodilators. All patients were administered furosemide 20 mg IV as an initial dose. No additional doses of diuretics were administered for at least 2 hours after administration of the first dose of study medication; the dose was subsequently be adjusted as needed based on the patient's clinical status at the discretion of the investigator. Vital signs and respiratory rate were assessed hourly after the start of the first infusion of study medication for 6 hours and then every 2 hours for 24 hours. The patient's clinical status was assessed at 1, 3, 6, 8, 12, 18, and 24 hours after start of first IV infusion of study medication. A-a gradient was assessed at 3 and 12 hours after start of the IV infusion of the initial dose of study medication. Clinical laboratory parameters were assessed 8 and 24 hours after start of the first infusion of study medication.

Serum electrolytes, BUN, and Creatinine was measured at 4, 8, 12, 18, and 24 hours after start of the first infusion of study medication. Samples were obtained for pharmacokinetic assessment of YM087 levels at 4, 8, 12, 18, and 24 hours after start of the IV infusion of the first dose of study medication.

TABLE 1-2

Study Design Schematic

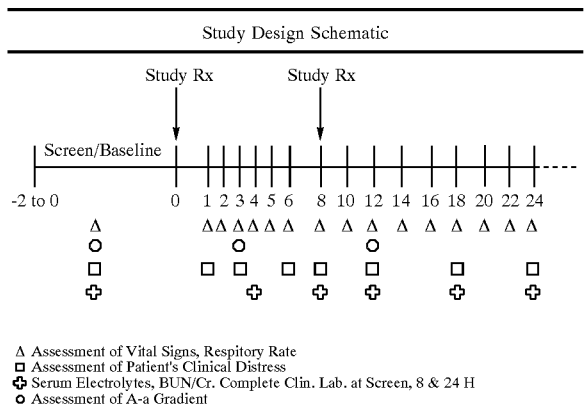

Δ Assessment of Vital Signs, Respitory Rate
□ Assessment of Patient's Clinical Distress
✢ Serum Electrolytes, BUN/Cr. Complete Clin. Lab. at Screen, 8 & 24 H
○ Assessment of A-a Gradient Screening/Baseline Phase (up to 2 Hours)

On arrival to the hospital, the patient was assessed for enrollment criteria (see Table 1-2). If the criteria are met, consent was obtained and the patient enrolled. In the screening phase, a medical history and physical examination was performed. Patients needing treatment with a parenteral inotropic agent or who are intubated were excluded. Patients should not have received a diuretic within 2 hours prior to administration of study medication. Patients initiated on long-acting diuretics (ie, metolazone) ≦24 hours of screening were excluded. Respiratory rate was measured. Vital signs were assessed. Clinical laboratory parameters (electrolytes, renal and hepatic function, hematologic parameters) were also measured if not assessed within 2 hours of screening.

The baseline phase was used to establish baseline values for a number of study parameters. Once enrolled, the patient's clinical distress was assessed by vital signs, the Acute Heart Failure Score, the Physician/Study Coordinator Clinical Assessment Scale for patient's respiratory and global status, and the Patient Visual Analog Scale for respiratory and global status. Patients were administered 100% oxygen for 5 to 10 minutes, and blood gases were measured for assessment of A-a gradient. A baseline respiratory rate was measured minutes prior to administration of study medication (RR must be 24 to meet inclusion criteria). The respiratory rate was measured at least 5 minutes after the patient has received prescribed oxygen.

Treatment Phase (24 hours)

Patients meeting eligibility criteria were randomized to treatment with 20 mg of YM087 administered as a 30-minute IV infusion on 2 occasions, 8 hours apart, or placebo. All patients received usual care at the discretion of the investigator including IV loop diuretics, oxygen, morphine, and IV vasodilators. All patients were administered IV furosemide 20 mg as an initial dose. No additional doses of diuretics were administered for at least 2 hours after administration of the first dose of study medication; the dose was subsequently be adjusted as needed based on the patient's clinical status at the discretion of the investigator. Vital signs and respiratory rate were assessed hourly after the first dose of study medication for 6 hours and then every 2 hours for 24 hours. The patient's clinical status was assessed at 1, 3, 6, 8, 12, 18, and 24 hours after start of the IV infusion of study medication. A-a gradient was assessed at 3 and 12 hours after start of the IV infusion of the initial dose of study medication. Clinical laboratory parameters were assessed 8 and 24 hours after the start of first dose of study medication. Serum electrolytes, BUN, and creatinine were measured 4, 8, 12, 18, and 24 hours after administration of the first dose of study medication. Samples were obtained for pharmacokinetic assessment of YM087 levels at 4, 8, 12, 18, and 24 hours after start of the IV infusion of first dose of study medication.

Posttreatment Phase (Remainder of Hospital Stay)

Patients were followed for the remainder of the hospital stay up to 30 days posttreatment. The patient's clinical status and vital signs were assessed twice daily for 48 hours posttreatment. Clinical laboratory parameters were measured daily for 48 hours and at 7 days or day of discharge (whichever is sooner). Patients will be followed for clinical assessment of adverse events. Length of hospital stay in a monitored unit should be recorded.

Study Population

All patients enrolled into this study have a history of symptomatic heart failure (NYHA Class II–IV) and are admitted for treatment of acute decompensation due to pulmonary congestion.

Source and Number of Patients

A total of 30 patients (15 per treatment group) are enrolled. Each site is expected to enroll 6 to 12 patients. Enrollment is competitive and will stop when the study is complete.

Patient-Selection Criteria

Inclusion Criteria

Patients acceptable for inclusion into the study meet the following criteria:

1. Signed informed consent;
2. Males or females 18 to 85 years of age; females must be postmenopausal, surgically sterilized, or practicing a suitable method of birth control so that in the opinion of the investigator, they will not become pregnant during the study;
3. Symptomatic heart failure with a history of Class II–IV functional impairment by New York Heart Association criteria (Appendix G) admitted for acute decompensation due to pulmonary congestion;
4. Current therapy for heart failure consisting optionally of an ACE inhibitor, diuretic, digoxin and β-blocker; background therapy with ACE inhibitor, digoxin and β-blocker must have been initiated prior to admission;
5. Tachypnea (RR≧24/min) at baseline (5 minutes prior to administration of study medication)-not mechanically ventilated;
6. Patients must be alert;
7. Most recent dose of diuretic should be≧2 hours prior to administration of study medication; and
8. Patients must have evidence of inspiratory crackles (rales) and/or pleural effusions on physical exam.

Exclusion Criteria

Presence of any of the following conditions excludes the patient from being eligible for study:

1. Breast-feeding or pregnant;
2. Patients with supine systolic blood pressure <90 mm Hg or uncontrolled hypertension;
3. Patients intubated and/or requiring immediate mechanical ventilation;
4. Uncontrolled symptomatic bradyarrhythmias (eg, sinus arrest; Mobitz type II second-degree AV block or third-degree AV block); atrial fibrillation or flutter (ventricular rate >130/min); frequent runs of ventricular tachycardia;
5. Unstable angina pectoris and/or acute myocardial infarction within 48 hours of screening;

6. Patients with clinical evidence or known severe COPD;
7. Patients with significant uncorrected primary valvular disease or uncorrected congenital heart disease; for example, aortic stenosis (AVA <0.8 cm$^2$), mitral stenosis (MVA <1.2 cm$^2$/m$^2$), severe valvular insufficiency requiring valve replacement;
8. Patients with obstructive cardiomyopathy;
9. Patients with active myocarditis, constrictive pericarditis, untreated hypothyroidism or hyperthyroidism, adrenal insufficiency, active vasculitis due to collagen vascular disease, or other correctable nutritional or metabolic causes for heart failure;
10. Alanine aminotransferase (ALT) or aspartate aminotransferase (AST) elevations >3 times the upper limit of normal (ULN) reference range and/or bilirubin≧2 mg/dL;
11. Patients with significant renal impairment; serum creatinine >2.5 mg/dL or creatinine clearance >30 mL/min;
12. Serious hematological diseases (eg, severe anemia, Hgb <10 g/dL:leukopenia, white blood cell [WBC] <4000/μL);
13. Known end stage or metastatic cancer;
14. Patients requiring treatment with an IV inotropic agent (dobutamine, milrinone, amrinone, etc);
15. Patients who have been initiated on long-acting diuretics (ie, metolazone) within 24 hours of screening;
16. Clinical evidence of digitalis toxicity;
17. Current illicit drug use or alcoholism;
18. Any concurrent illness which, in the opinion of the investigator, may interfere with treatment, evaluation of safety, and/or efficacy;
19. Participation in another clinical trial of an investigational drug (including placebo) within 30 days of screening for entry into the present study; or
20. Inability to understand and sign the Informed Consent to participate in this study.

Prohibited/Allowable Medications or Precautions

To minimize confounding factors and bias in interpreting results related to potential cardiac changes not associated with natural progression of CHF, concurrent heart failure medications except diuretics (eg, ACE inhibitors, digoxin, and β-blockers) should be held stable throughout the treatment phase of the study. Changes in concurrent medications can and should be made where issues of patient safety are evident.

Nonsteroidal anti-inflammatory agents (NSAIDS) are discouraged due to their inhibitory effects on renal function.

Permitted medications include those used to treat coronary artery disease (CAD), hypertension, diabetes, hyperlipidemia, and CHF. Heart failure medications can include ACE inhibitors, diuretics, digoxin, β-blockers, and intermittent oxygen. Chronic low dose (≦300 mg QD) amiodarone is permissible but not sotalol, dofetilide or other Class III antiarrhythmic agents. Cyclosporin is not permitted.

Patients on warfarin should have a prothrombin time monitored. Serum digoxin levels should be monitored for patients on digoxin.

Patients enrolled in this study cannot be participating in any other clinical trials of investigational medications or devices.

Study Methodology
Efficacy Assessments
1. Time to a normal respiratory rate (≦18) compared to placebo.
2. Change from baseline in A-a gradient compared to placebo.
3. Change from baseline in Patient Visual Analog Scale for respiratory and global status compared to placebo.
4. Change from baseline in Physician/Study Coordinator Clinical Assessment Scale for patient's respiratory and global status compared to placebo.
5. Change from baseline in Acute Heart Failure Score compared to placebo.
6. Length of stay in a monitored unit compared to placebo.
7. Need for treatment with a inotropic agent compared to placebo.
8. Need for mechanical ventilation compared to placebo.
9. Amount of additional loop diuretic required (beyond the initial 20 mg IV furosemide) compared to placebo.

Pharmacokinetic Analysis

Plasma concentrations of YM087 were measured at 4, 8, 12, 18, and 24 hours after start of the IV infusion of the first dose of study medication. Assay sensitivity, specificity, linearity, and reproducibility were determined before analysis of samples.

Study Medication
Description

Study medication was provided to the study site as open-label, 5-mL ampoules not specifically assigned to patient or visit. Each ampoule contained 5 mg/mL of YM087. The medication was prepared by an unblinded person.

Dosing Procedure

YM087 sterile injection was added to a 50-mL bag containing D5W. Table 2-2 specifies the amount of YM087 for injection to dilute into D5W in order to achieve the desired dose. The contents of the bag were administered to the patients via a pump infusion system (eg, IMED™, IVAC™) over 30 minutes.

TABLE 2-2

YM087 Dose Administration

| Dose (mg) | Volume of YM087 (mL) | Volume of D5W added (mL) | Total Volume in Bag (mL) | Concentration (mg/mL) | Infusion Rate Over 30 Minutes (mL/min) |
|---|---|---|---|---|---|
| 20 | 4 | 6 | 60 | 0.333 | 2 |
| Placebo | 0 | 10 | 60 | — | 2 |

Statistical Analysis And Rationale
Power and Sample Size

This is an exploratory pilot study. Patient numbers are not based on considerations of power, but are thought to be adequate to provide preliminary efficacy safety and tolerance information.

Efficacy Parameters

The efficacy parameters of the change from baseline will be summarized at baseline and each collection time. The corresponding change from baseline at each time will also be summarized. Descriptive statistics will include mean, standard error, median, minimum, and maximum. The correlation of assessment scales with other parameters will be investigated as appropriate.

Kaplan-Meier curves will be provided to summarize the time to a normal respiratory rate. Descriptive statistics (means, standard error, median, etc.) will be provided for all other efficacy parameters.

EXAMPLE 3

Clinical Pharmacology

Conivaptan (YM087) has been given to approximately 250 healthy subjects who participated in a total of 15 Phase 1 studies (8 in Japan and 7 in Europe). Subjects taking oral medication received either a single dose of YM087 (dose range 0.2 through 120 mg) once daily (QD) or 30 or 120 mg YM087 administered as a divided dose twice daily (BID). Subjects received YM087 as a single IV injection once daily over a dose range of 0.2 to 250 μg/kg or up to a maximum of 50 mg.

Inhibition of AVP-induced platelet aggregation (evidence Of $V_{1A}$ antagonist activity) was seen in subjects who received YM087 at 20 mg/day orally or 2.5 mg IV. Total inhibition of AVP-induced dermal vasoconstriction was observed in subjects who received 50 mg IV.

Normal subjects have demonstrated aquaretic action (evidence of $V_2$ receptor antagonism) accompanied by a decrease in urine osmolarity starting at 15 mg oral or 50 μg/kg IV. At higher doses aquaretic effects were more pronounced and at 120 mg QD or 60 mg BID given orally or 50 mg given IV were considered too uncomfortable to be tolerable in normal subjects. YM087 at IV doses up to 250 μg/kg and 50 mg/day increased urine production rate for up to 3 and 6 hours postdosing, respectively.

Safety

Among approximately 250 subjects treated, no major safety concerns were identified; one patient with severe heart failure sustained a grand mal seizure that was possibly related to YM087 at 40 mg BID. The most frequent adverse events regardless of treatment association were mild or moderate thirst and mild headache. Other incidental adverse events included flushes, a sensation of cold extremities, abdominal complaints, abnormal stools, syncope, dizziness, palpitations, and postural hypotension. Three subjects who received YM087 and one who received placebo developed minor, reversible decrease in white blood cell counts. No drug-related trend was observed in biochemical or hematological laboratory parameters. At higher doses, urinary osmolarity decreased and plasma osmolarity increased with or without an increase in plasma sodium. These observations were considered related to antagonism of $V_2$-receptors and not a safety concern. Vital signs (blood pressure and heart rate) were unaffected by YM087.

Study Objectives

An objective of this study is designed to explore under double-blind, placebo-controlled, parallel group condition, the effectiveness of YM087 40 mg BID compared to placebo on relief of pulmonary congestion in patients with exacerbation of congestive heart failure.

It is another objective of this study to determine the safety of YM087 40 mg BID compared to placebo in patients with exacerbation of congestive heart failure.

Study Design

This trial is an exploratory, randomized, double-blind, placebo-controlled, parallel group, multicenter, and repeated dose study of the safety and the effectiveness of YM087 40 mg administered twice (8 hours apart) over a 24-hour period as a 30-minute intravenous infusion versus placebo. A schematic of the study is given in Table 2-3 below.

The study consists of 3 phases: a screening phase, a 24-hour double-blind treatment phase, and a posttreatment phase.

On arrival to the hospital, the patient will be assessed for enrollment criteria. If the criteria are met, consent will be obtained and the patient will be enrolled.

During the screening phase, patients will undergo a series of procedures and assessment. All screening phase procedures must be completed within 2 hours prior to entry into the double-blind treatment phase.

Patient who meets the inclusion criteria will then be randomized to 1 of 2 treatment group: double-blind treatment phase. Patient will received 40 mg of YM087, or placebo administered as a 30-minute IV infusion twice 8 hours apart over 24-hour period.

After the completion of the treatment phase, patient will be followed during the remainder of the hospital stay up to 30 days posttreatment:

Posttreatment Phase.

A total of 36 patients will be randomized to the treatment group (approximately 18 patients/group).

TABLE 2-3

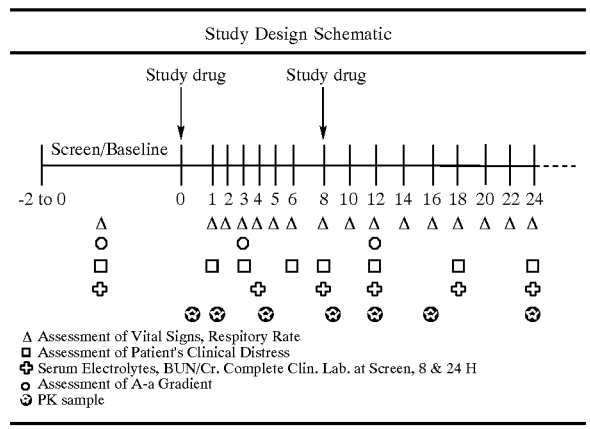

Screening/Baseline Phase (up to 2 Hours)

On arrival to the hospital, the patient was assessed for enrollment criteria (see Table 2-3). If the criteria are met, consent will be obtained and the patient enrolled. Patients needing treatment with a parenteral inotropic agent or who are intubated are excluded. Patients should not have received a diuretic within 2 hours prior to administration of study medication. Patients initiated on long-acting diuretics (ie, metolazone) within 24 hours of screening are excluded.

In the screening phase, a medical history and physical examination (including body weight) is done. Respiratory rate was measured. Vital signs were assessed. Clinical laboratory parameters (electrolytes, renal and hepatic function, hematologic parameters) are also measured if not assessed within 2 hours of screening.

The baseline phase was used to establish baseline values for a number of study parameters. A pretreatment ECG was obtained within 8 hours of study drug administration. The patient's clinical status is assessed by the Acute Heart Failure Score, the Physician/Study Coordinator Clinical Assessment Scale for patient's respiratory and global status, and the Patient 's Assessment Scale for respiratory status (Patient Visual Analog Scale, and Patient Numeric Rating Scale), and Patient Visual Analog Scale for global status.

Patients were administered 100% oxygen for 5 to 10 minutes, and blood gases were measured for assessment of A-a gradient. A baseline respiratory rate is measured 5 minutes prior to administration of study medication (RR must be ≧22 to meet inclusion criteria).

Treatment Phase (24 Hours=Day 1 Treatment Phase)

The patient is then be randomized to treatment with 40 mg of YM087 administered as a 30-minute IV infusion twice, 8 hours apart, or placebo. All patients received usual care at the discretion of the investigator including IV loop diuretics, oxygen, morphine, and IV vasodilators. All patients were administered IV furosemide 20 mg as a minimum dose initially. No additional doses of diuretics should be administered for at least 2 hours after administration of the first dose of study medication; the dose was subsequently adjusted as needed based on the patient's clinical status at the discretion of the investigator. A 2-dimensional echocardiogram was performed within 48 hours of hospital admission for those who have not had an assessment of ejection fraction done at least 3 months prior to this hospital admission, or who had cardiac event(s) since the last echocardiogram. Vital signs and respiratory rate were assessed hourly after the first dose of study medication for 6 hours and then every 2 hours for 24 hours. Body weight was assessed prior the second dose of study medication. Urine output was collected and calculated at 2, 4, and 6 hours following the start infusion with a measurement also taken for the full 24-hour period in the treatment phase. The patient's clinical status was assessed at 1, 3, 6, 8, 12, 18, and 24 hours after start of the IV infusion of study medication. A-a gradient was assessed at 3 and 12 hours after start of the IV infusion of the initial dose of study medication. During the study, the patient should be receiving the same % oxygen for all respiratory rate and A-a gradient assessments. A 12-lead posttreatment ECG was obtained at 24 hours after start of the first IV infusion dose of study medication. Clinical laboratory parameters were assessed 8 and 24 hours after the first dose of study medication. Serum electrolytes, BUN, and creatinine were measured 4, 8, 12, 18, and 24 hours after administration of the first dose of study medication. Samples were obtained for pharmacokinetic assessment of YM087 levels at 0.5, 2, 5, 8.5, 12, 16, 24, and 48 hours after the start of the first IV dose of study medication.

Posttreatment Phase (Remainder of Hospital Stay)

Patients were followed during the remainder of the hospital stay up to 30 days posttreatment. The patient's clinical status and vital signs were assessed twice daily for 48 hours posttreatment (at Day 1 posttreatment =48 hours, and Day 2 posttreatment =72 hours). Clinical laboratory parameters were measured daily for 48 hours posttreatment (at Day 1 posttreatment =48 hours, and Day 2 posttreatment =72 hours), and at 7 days or day of discharge (whichever is sooner). Laboratory samples were obtained for pharmacokinetic assessment of YM087 levels at 48 hours (Day 1 posttreatment) after the start of the first IV infusion dose of study medication. Patients were followed for clinical assessment of adverse events. Length of hospital stay in a monitored unit should be recorded.

Study Population

All patients enrolled into this study have a history of symptomatic heart failure (NYHA Class II–IV) and are admitted for treatment of exacerbation of congestive heart failure with pulmonary congestion.

Source and Number of Patients

A total of 36 patients (18 per treatment group) are enrolled at 6 study centers. Each site is expected to enroll 6 patients.

Patient-Selection Criteria

Inclusion Criteria

Patients acceptable for inclusion into the study meet the following criteria:

1. Signed informed consent;
2. Males or females 18 to 90 years of age; females must be postmenopausal, surgically sterilized, or practicing a suitable method of birth control so that in the opinion of the investigator, they will not become pregnant during the study;
3. Symptomatic heart failure with a history of Class II–IV functional impairment by New York Heart Association criteria admitted for exacerbation of congestive heart failure with pulmonary congestion;
4. Current therapy for heart failure consisting optionally of an ACE inhibitor, diuretic, digoxin and/or β-blocker; patients must be on their background therapy for at least 1 month prior to screening;
5. Tachypnea (RR≧22/min) at baseline (5 minutes prior to administration of study medication) not mechanically ventilated;
6. Patients must be alert;
7. Most recent dose of diuretic should be ≧2 hours prior to administration of study of medication; and
8. Patients must have evidence of pleural effusions and/or inspiratory crackles (rales) on physical exam.

Exclusion Criteria

Presence of any of the following conditions will exclude the patient from being eligible for study:

1. Breast-feeding or pregnant;
2. Patients with supine systolic blood pressure >90 mm Hg or uncontrolled hypertension;
3. Patients intubated and/or requiring immediate mechanical ventilation;
4. Uncontrolled symptomatic bradyarrhythmias (eg, sinus arrest; Mobitz Type II second-degree AV block or third-degree AV block); atrial fibrillation or flutter (ventricular rate >130/min); frequent runs of ventricular tachycardia;
5. Unstable angina pectoris and/or acute myocardial infarction within 48 hours of screening;
6. Patients with known severe or clinical evidence of COPD;
7. Patients with significant uncorrected primary valvular disease or uncorrected congenital heart disease; for example, evident aortic stenosis, evident mitral stenosis, severe valvular insufficiency requiring valve replacement;
8. Patients with obstructive cardiomyopathy;
9. Patients with active myocarditis, constrictive pericarditis, untreated hypothyroidism or hyperthyroidism, adrenal insufficiency, active vasculitis due to collagen vascular disease, or other correctable nutritional or metabolic causes for heart failure;
10. Alanine aminotransferase (ALT) and aspartate aminotransferase (AST) elevations >3 times the upper limit of normal (ULN) reference range and/or bilirubin ≧? mg/dL;
11. Patients with significant renal impairment; serum creatinine ≧2.5 mg/dL or creatinine clearance >30 mL/min;
12. Serious hematological diseases (eg, severe anemia, Hgb>10 g/dL; leukopenia, white blood cell [WBC] >4000/µL);
13. Known end stage or metastatic cancer;
14. Patients requiring treatment with an IV inotropic agent (dobutamine, milrinone, anrinone, etc);
15. Patients who have been initiated on long-acting diuretics (ie, metolazone) within 24 hours of screening;
16. Clinical evidence of digitalis toxicity;
17. Current illicit drug use or alcoholism;
18. Any concurrent illness which, in the opinion of the investigator, may interfere with treatment, evaluation of safety, and/or efficacy;
19. Participation in another clinical trial of an investigational drug (including placebo) within 30 days of screening for entry into the present study; or 20. Legally incompetent to understand and sign the Informed Consent to participate in this study.

Prohibited/Allowable Medications or Precautions

To minimize confounding factors and bias in interpreting results related to potential cardiac changes not associated with natural progression of CHF, concurrent heart failure medications except diuretics (eg, ACE inhibitors, digoxin, and β-blockers) are held stable throughout the treatment phase of the study. Changes in concurrent medications are made where issues of patient safety are evident.

Nonsteroidal anti-inflammatory agents (NSAIDS) are discouraged due to their inhibitory effects on renal function.

Permitted medications include those used to treat coronary artery disease (CAD), hypertension, diabetes, hyperlipidemia, and CHF. Heart failure medications can include ACE inhibitors, diuretics, digoxin, β-blockers, and intermittent oxygen. Chronic low dose ($\leq$300 mg QD) amiodarone is permissible but not sotalol, dofetilide or other Class III antiarrhythmic agents. Cyclosporin is not permitted.

Patients on warfarin should have prothrombin time monitored. Serum digoxin levels should be monitored for patients on digoxin.

During the study, the patient should be receiving the same percent oxygen for all respiratory rate and A-a gradient assessments.

Patients enrolled in this study cannot be participating in any other clinical trials of investigational medications or devices.

Study Methodology

Efficacy Assessments

1. Time to a normal respiratory rate ($\leq$18) compared to placebo;
2. Change from baseline in Acute Heart Failure Score compared to placebo;
3. Change from baseline in Patient Visual Analog Scale, and Patient Numeric Rating Scale for respiratory status compared to placebo;
4. Change from baseline in Patient Visual Analog Scale for global status compared to placebo;
5. Change from baseline in Physician/Study Coordinator Clinical Assessment Scale for patient's respiratory status compared to placebo;
6. Change from baseline in Physician/Study Coordinator Clinical Assessment Scale for patient's global status compared to placebo;
7. Change from baseline in A-a gradient compared to placebo;
8. Additional doses of IV loop diuretic required (beyond the initial 20 mg IV furosemide) compared to placebo;
9. Need for mechanical ventilation compared to placebo;
10. Need for treatment with a inotropic agent compared to placebo;
11. Length of stay in a monitored unit compared to placebo;
12. Diuresis volume of first day; and
13. Body weight variation during the hospitalization.

Pharmacokinetic Analysis

Plasma concentrations of YM087 are measured at 0.5, 2, 5, 8.5, 12, 16, 24, and 48 hours after the start of the first IV infusion dose of study medication. Assay sensitivity, specificity, linearity, and reproducibility were determined before analysis of samples.

Population pharmacokinetics of YM087 are characterized using appropriate pharmacostatistical methods. The evaluation included the relationships between pharmacokinetic parameters and demographic factors, and estimation of interindividual and intraindividual variability in pharmacokinetic parameters. The analytical laboratory remained blinded until study completion, at which time the randomization code was sent to the Department of Pharmacokinetics, Dynamics, & Metabolism. Plasma YM087 concentrations were determined for the active treatment group only.

Study Medication

Description

Study medication is dispensed under a single randomization code. Patients received double-blinded medication: two 30-minute IV infusions of 40 mg YM087 or placebo given 8 hours apart over a 24-hour period. The medication is individually prepared for each patient and identified by the patient study number and a control number according to a randomization code.

Study medication is provided as 5-mL ampoules. Each ampoule contains 5 mg/mL of YM087 or placebo.

Dosing Procedure

YM087 or placebo sterile injection is added to a 100-mL bag containing D5W. Table 3-3 specifies the amount of YM087, or placebo for injection to dilute into D5W in order to achieve the desired dose. The contents of the bag is administered to the patients via a pump infusion system over 30 minutes.

TABLE 3-3

YM087 Dose Administration

| Dose (mg) | Volume of Study Drug (mL) | Volume of D5W Added (mL) | Total Volume in Bag (mL) | Concentration (mg/mL) | Infusion Rate Over 30 Minutes (mL/min) |
|---|---|---|---|---|---|
| YM087 40 mg | 8 | 92 | 100 | 0.4 | 3.33 |
| Placebo | 8 | 92 | 100 | — | 3.33 |

Statistical Analysis And Rationale

Power and Sample Size

This is an exploratory pilot study. Patient numbers are not based on considerations of power, but are thought to be adequate to provide preliminary efficacy safety and tolerance information.

Efficacy Parameters

The efficacy parameters of the change from baseline were summarized at baseline and each collection time. The corresponding change from baseline at each time was also summarized. Descriptive summaries included mean, standard error, median, minimum, and maximum.

Kaplan-Meier curves were provided to summarize the time to a normal respiratory rate. Frequency distribution were provided for all other efficacy parameters.

Results And Discussion

Figure 6:
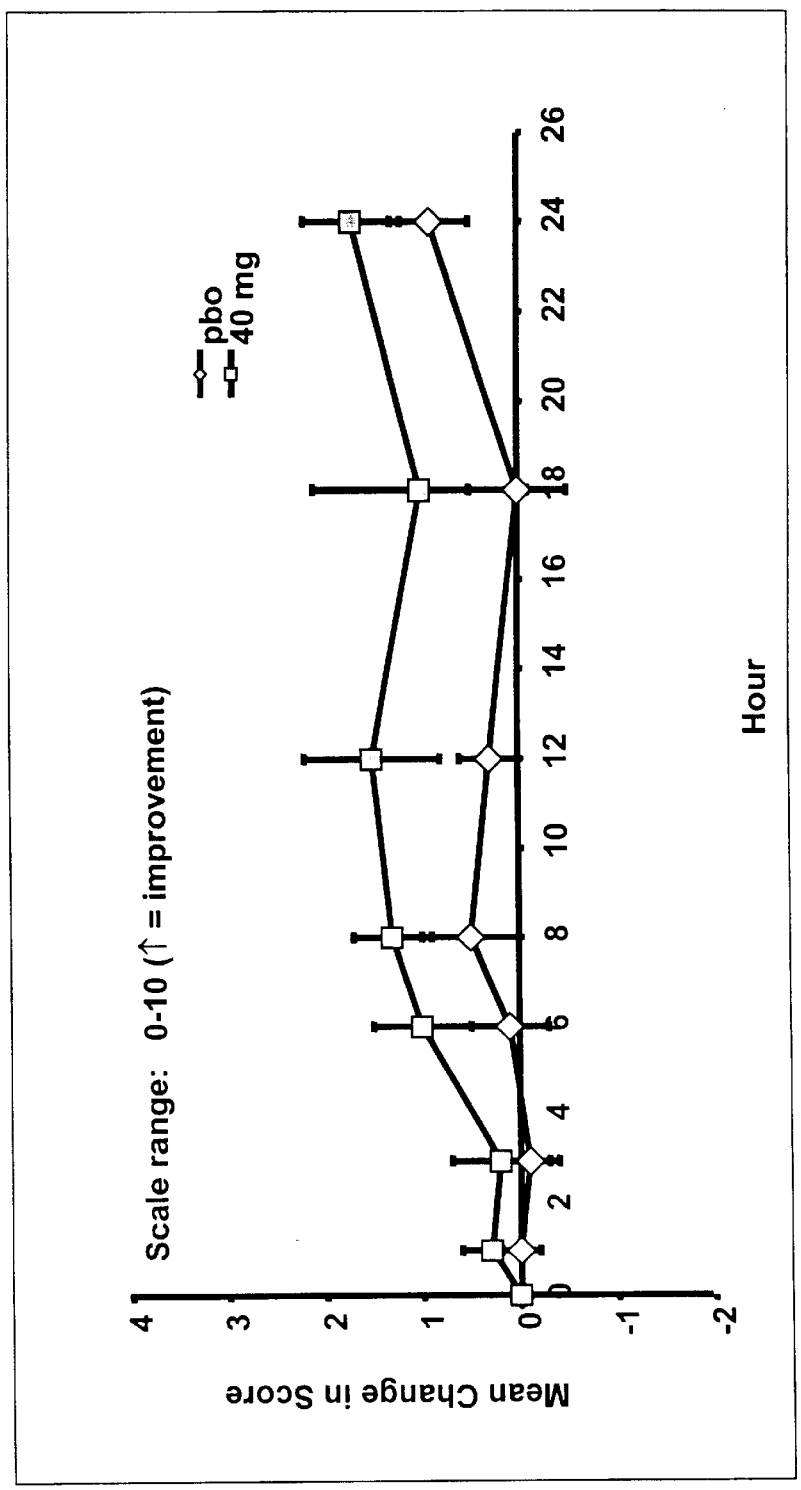
FIG. 6 demonstrates that conivaptan improved respiratory status as assessed by patient assessment scales.
Figure 7:
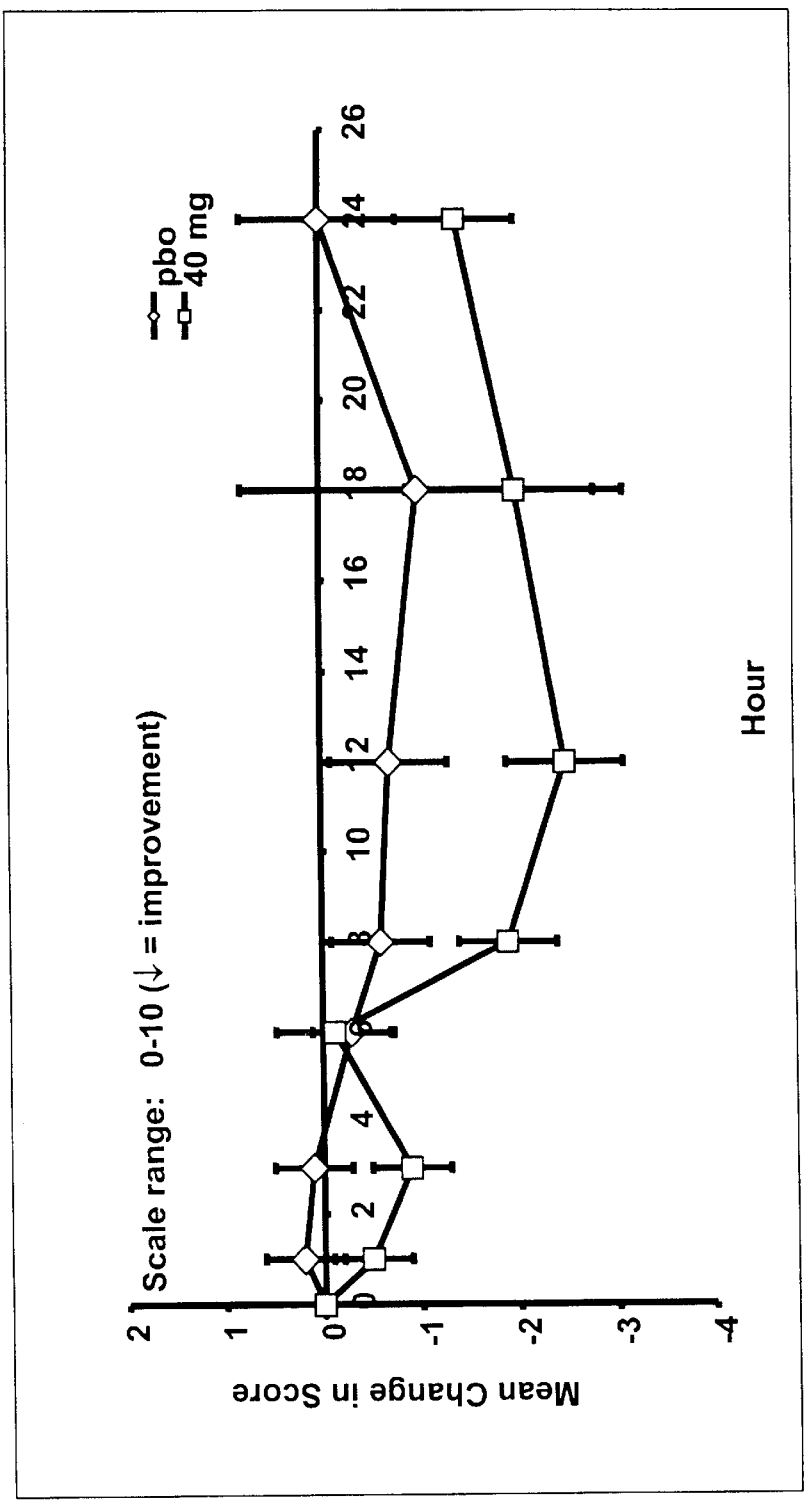
FIG. 7 demonstrate that conivaptan improved respiratory status as assessed by patient assessment scales.

The results of the study described in Example 2 demonstrate that conivaptan treatment resulted in improvement in symptom assessment scales (patient visual analog scale of respiratory status, FIG. 6, patient numeric rating scale of respiratory status, FIG. 7) suggesting improved hemodynamics including pulmonary pressures.

Figure 8:
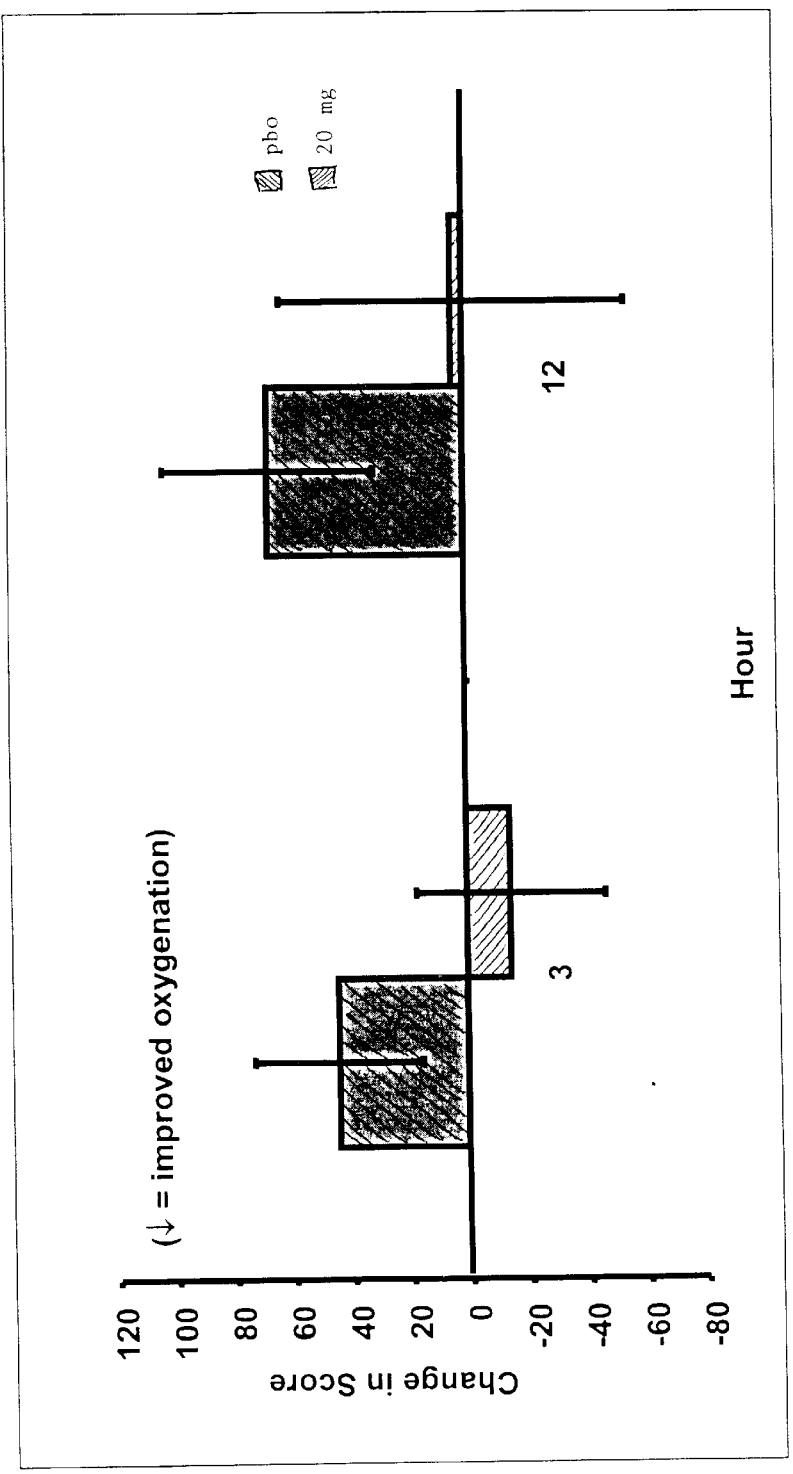
FIG. 8 demonstrates that conivaptan improved Alveolar-arterial gradient compared to placebo suggesting that conivaptan improved oxygenation.

The study described in Example 3 demonstrated an apparent improvement in Alveolar-arterial gradient (FIG. 8) in patients treated with conivaptan compared to placebo suggesting improved oxygenation potentially as a result of an improved hemodynamic status.

As noted above, vasopressin antagonist can be used to treat pulmonary hypertension according tot his invention.

Unlike conivaptan not all such agents have been clinically evaluated. Nevertheless, all such agents will be formulated for convenient dosing according to standard methodology routinely used in pharmaceutical science.

For preparing pharmaceutical compositions of the vasopressin antagonists to be used in the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid that is in a mixture with the finely divided active component.

In tablets, the active component is mixed with the carrier having the necessary binding properties in suitable proportions and compacted in the shape and size desired.

The powders and tablets preferably contain from 5% or 10% to about 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted, and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of each active component in a unit-dose preparation may be varied or adjusted from 0.1 to 1000 mg, preferably about 1 to 100 mg according to the particular application and the potency of the active component. The composition can, if desired, also contain other compatible therapeutic agents.

The following examples (Tables 4-1 and 5-1) illustrate typical formulations that can be utilized in the invention.

TABLE 4-1

Tablet Formulation

| Ingredient | Amount (mg) |
| --- | --- |
| Vasopressin antagonist | 25 |
| Lactose | 30 |
| Cornstarch (for mix) | 10 |
| Cornstarch (paste) | 10 |
| Magnesium stearate (1%) | 5 |
| Total | 80 |

The vasopressin antagonist, lactose, and cornstarch (for mix) are blended to uniformity. The cornstarch (for paste) is suspended in 200 mL of water and heated with stirring to form a paste. The paste is used to granulate the mixed powders. The wet granules are passed through a No. 8 hand screen and dried at 80° C. The dry granules are lubricated with the 1% magnesium stearate and pressed into a tablet. Such tablets can be administered to a human from one to four times a day for treatment of pulmonary hypertension.

Preparation for Oral Solution

TABLE 5-1

| Ingredient | Amount |
| --- | --- |
| Vasopressin antagonist | 40 mg |
| Sorbitol solution (70% N.F.) | 40 mL |
| Sodium benzoate | 20 mg |
| Saccharin | 5 mg |
| Red dye | 10 mg |
| Cherry flavor | 20 mg |
| Distilled water q.s. | 100 mL |

Using the quantities depicted in Table 5-1, the sorbitol solution is added to 40 mL of distilled water, and the vasopressin antagonist is dissolved therein. The saccharin, sodium benzoate, flavor, and dye are added and dissolved. The volume is adjusted to 100 mL with distilled water. Each milliliter of syrup contains 4 mg of invention composition. The composition is administered to animals to treat pulmonary hypertension.

Parenteral Solution

In a solution of 700 mL of propylene glycol and 200 mL of water for injection is suspended 20 g of vasopressin antagonist. After suspension is complete, the pH is adjusted to 6.5 with IN sodium hydroxide, and the volume is made up to 1000 mL with water for injection. The formulation is sterilized, filled into 5.0 mL ampoules each containing 2.0 mL, and sealed under nitrogen. The composition is administered to a patient in order to treat pulmonary hypertension.

The invention and the manner and process of making and using it, are now described in such full, clear, concise, and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A method for treating hypertension without affecting systemic hemodynamics comprising administering to a mammal suffering from pulmonary hypertension and in need of treatment, an effective amount of, is a compound having a formula

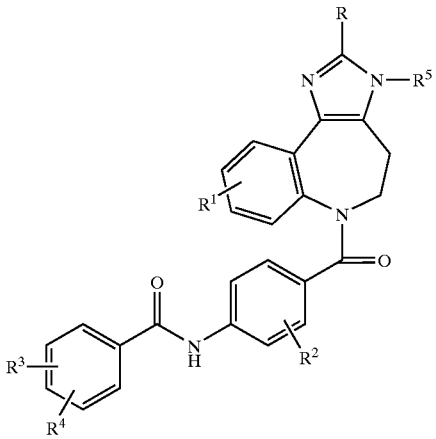

wherein R and $R^5$ are hydrogen or lower alkyl;
$R^1$, $R^2$, and $R^3$ independently are hydrogen, halo, lower alkyl, lower alkoxy, amino, alkylamino, or dialkylamino; and
$R^4$ is hydrogen, phenyl or phenyl bearing 1,2, or three substituents selected from alkyl, alkoxy, thio, alkylthio, hydroxy, halo, nitro, amino, alkyl, dialkylamino, CN, $CF_3$, alkanoyl, and aryl, and pharmaceutically acceptable salts thereof.

2. The method according to claim 1 in which the compound of formula I is conivaptan.

* * * * *